US012630871B2

(12) United States Patent
Nerenberg et al.

(10) Patent No.: US 12,630,871 B2
(45) Date of Patent: May 19, 2026

(54) METHODS AND SYSTEMS FOR DETECTING TISSUE CONDITIONS

(71) Applicant: Superfluid Dx, Inc., South San Francisco, CA (US)

(72) Inventors: Michael Nerenberg, Del Mar, CA (US); Neeraj Salathia, La Jolla, CA (US); Arkaitz Ibarra, San Diego, CA (US); Yue Zhao, San Diego, CA (US)

(73) Assignee: SUPERFLUID DX, INC., South San Francisco, CA (US)

( * ) Notice: Subject to any disclaimer, the term of this patent is extended or adjusted under 35 U.S.C. 154(b) by 700 days.

(21) Appl. No.: 17/898,112

(22) Filed: Aug. 29, 2022

(65) Prior Publication Data

US 2023/0399685 A1 Dec. 14, 2023

Related U.S. Application Data

(63) Continuation of application No. 17/579,878, filed on Jan. 20, 2022, now abandoned, which is a continuation of application No. 16/824,413, filed on Mar. 19, 2020, now abandoned, which is a continuation of application No. PCT/US2018/051674, filed on Sep. 19, 2018.

(60) Provisional application No. 62/560,936, filed on Sep. 20, 2017.

(51) Int. Cl.
| | |
|---|---|
| *C12Q 1/6851* | (2018.01) |
| *C12N 15/10* | (2006.01) |
| *C12Q 1/6806* | (2018.01) |

(52) U.S. Cl.
CPC ....... *C12Q 1/6851* (2013.01); *C12N 15/1006* (2013.01); *C12Q 1/6806* (2013.01)

(58) Field of Classification Search
CPC ............... C12Q 1/6851; C12Q 1/6806; C12Q 2545/10; C12Q 2563/131; C12N 15/1006; G01N 2333/70589; G01N 2333/70596; G01N 33/53; A61K 35/16
See application file for complete search history.

(56) References Cited

U.S. PATENT DOCUMENTS

| | | | |
|---|---|---|---|
| 5,432,054 | A | 7/1995 | Saunders et al. |
| 5,629,147 | A | 5/1997 | Asgari et al. |
| 6,664,056 | B2 | 12/2003 | Lo et al. |
| 7,235,359 | B2 | 6/2007 | Lo et al. |
| 7,713,693 | B1 | 5/2010 | Shah |
| 7,829,285 | B2 | 11/2010 | Lo et al. |
| 10,240,200 | B2 | 3/2019 | Koh et al. |
| 2002/0045176 | A1 | 4/2002 | Lo et al. |
| 2006/0003342 | A1 | 1/2006 | Bianchi et al. |
| 2006/0166242 | A1 | 7/2006 | Pennell et al. |
| 2009/0318304 | A1 | 12/2009 | Drmanac et al. |
| 2010/0056384 | A1 | 3/2010 | Hobbs et al. |
| 2010/0145131 | A1 | 6/2010 | Grinberg-Rashi et al. |
| 2011/0003294 | A1 | 1/2011 | Liew |
| 2011/0008805 | A1 | 1/2011 | Urdea et al. |
| 2011/0076751 | A1* | 3/2011 | Fabis ................. C12N 15/1003 435/270 |
| 2011/0144076 | A1 | 6/2011 | Williams et al. |
| 2011/0150775 | A1 | 6/2011 | Slonim et al. |
| 2011/0263441 | A1 | 10/2011 | Golub et al. |
| 2012/0129708 | A1 | 5/2012 | Bale et al. |
| 2012/0172251 | A1 | 7/2012 | Lowes |
| 2013/0252835 | A1 | 9/2013 | Koh et al. |
| 2013/0337440 | A1* | 12/2013 | Antes ..................... G01N 33/52 435/6.1 |
| 2015/0065355 | A1 | 3/2015 | Meder et al. |
| 2015/0182588 | A1 | 7/2015 | Kahvejian et al. |
| 2016/0333338 | A1 | 11/2016 | Haj-Ahmad et al. |
| 2017/0248508 | A1* | 8/2017 | Ward ................. G01N 33/5091 |
| 2019/0071795 | A1 | 3/2019 | Nerenberg et al. |
| 2020/0270698 | A1 | 8/2020 | Koh et al. |
| 2021/0047752 | A1 | 2/2021 | Nerenberg et al. |
| 2021/0054445 | A1 | 2/2021 | Nerenberg et al. |
| 2023/0349073 | A1 | 11/2023 | Nerenberg et al. |

FOREIGN PATENT DOCUMENTS

| | | |
|---|---|---|
| CA | 2838562 A1 | 2/2013 |
| WO | WO-03044536 A1 | 5/2003 |
| WO | WO-2004065629 A1 | 8/2004 |
| WO | WO-2006011363 A1 | 2/2006 |
| WO | WO-2007103572 A2 | 9/2007 |
| WO | WO-2009025852 A2 | 2/2009 |
| WO | WO-2009093254 A2 | 7/2009 |
| WO | WO-2009117122 A2 | 9/2009 |

(Continued)

OTHER PUBLICATIONS

Andreu, Zoraida et al. Comparative analysis of EV isolation procedures for miRNAs detection in serum samples. Journal of extracellular vesicles vol. 5 31655. Jun. 20, 2016.
Cahoy, JD et al. A transcriptome database for astrocytes, neurons, and oligodendrocytes: a new resource for understanding brain development and function. Journal of Neuroscience 28(1):264-278 (Jan. 2, 2008).
Chaussabel, D. et al. A modular analysis framework for blood genomics studies: application to systemic lupus erythematosus. Immunity, 29(1):150-164 (Jul. 18, 2008).

(Continued)

*Primary Examiner* — Cynthia B Wilder
(74) *Attorney, Agent, or Firm* — WILSON SONSINI GOODRICH & ROSATI

(57) ABSTRACT

Provided herein are methods and systems for detecting tissue conditions. In some aspects, levels of one or more markers of a disease or condition and one or more tissue-specific cell-free polynucleotides are quantified, levels are compared to a reference, and it is determined whether the tissue has been damaged by the disease or condition based on the comparing. Systems for performing the methods described herein are also provided.

23 Claims, 15 Drawing Sheets

Specification includes a Sequence Listing.

(56) References Cited

FOREIGN PATENT DOCUMENTS

| WO | WO-2010072410 A2 | 7/2010 | |
| WO | WO-2011071893 A1 | 6/2011 | |
| WO | WO-2011154940 A1 | 12/2011 | |
| WO | WO-2011156734 A2 | 12/2011 | |
| WO | WO-2012004371 A2 | 1/2012 | |
| WO | WO-2012012693 A2 | 1/2012 | |
| WO | WO-2012155014 A1 | 11/2012 | |
| WO | WO-2013007708 A1 | 1/2013 | |
| WO | WO-2013049674 A1 | 4/2013 | |
| WO | WO-2013113012 A2 | 8/2013 | |
| WO | WO-2013176741 A1 | 11/2013 | |
| WO | WO-2014150198 A2 | 9/2014 | |
| WO | WO-2016007755 A1 | 1/2016 | |
| WO | WO-2016022654 A1 | 2/2016 | |
| WO | WO-2016187234 A1 | 11/2016 | |
| WO | WO-2016196945 A1 | 12/2016 | |
| WO | WO-2017035262 A1 | 3/2017 | |
| WO | WO-2017139553 A1 | 8/2017 | |
| WO | WO-2017156310 A1 | 9/2017 | |
| WO | WO-2017197399 A1 * | 11/2017 | ......... C12N 15/1006 |
| WO | WO-2019060369 A1 | 3/2019 | |

OTHER PUBLICATIONS

Chen, Chihchen et al. Microfluidic isolation and transcriptome analysis of serum microvesicles. Lab on a chip vol. 10,4 (2010): 505-11.

Co-pending U.S. Appl. No. 17/579,878, inventors Nerenberg; Michael et al., filed Jan. 20, 2022.

Segal, E. et al. Module networks: identifying regulatory modules and their condition-specific regulators from gene expression data. Nature Genetics, 34(2):166-176 (Jun. 2003).

EP17764127.1 Extended European Search Report dated Aug. 2, 2019.

EP18859705.8 Extended European Search Report dated Jun. 14, 2021.

Geekiyanage, et al. Blood serum miRNA: Non-invasive biomarkers for Alzheimer's disease. Exp Neurol. Jun. 2012; 235(2): 491-496.

Goldenberg, Robert L. et al., Biochemical markers for the prediction of preterm birth. American Journal of Obstetrics and Gynecology, 192(5) S36-46:3007-3019 (2005).

Goldfarb, et al. Dual and primal-dual methods for solving strictly convex quadratic programs. In: Hennart J.P. (eds) Numerical Analysis. Lecture Notes in Mathematics, vol. 909. Springer, Berlin, Heidelberg. 1982; pp. 226-239.

Goldfarb, et al. A numerically stable dual method for solving strictly convex quadratic programs. Mathemtical Programming, 1983 (27); pp. 1-33.

Grosios, Konstantina, et al. Overview of healthcare in the UK. The EPMA Journal 1 (2010): 529-534.

Human Protein Atlas, (primary reference Uhlen et al. Proteomics. Tissue-based map of the human proteome. Science, 347:6220 (Jan. 23, 2015), retrieved from the internet between Mar. 21 to Mar. 30, 2016.

International Application No. PCT/US13/23471 International Search Report and Written Opinion for Issued Apr. 11, 2013.

International Application No. PCT/US2017/021637 International Preliminary Report on Patentability Mailed Sep. 11, 2018.

International Application No. PCT/US2017/021637 International Search Report and Written Opinion Mailed Jun. 6, 2017.

Ishigaki et al. Differentially expressed genes in sporadic amyotrophic lateral sclerosis spinal cords—screening by molecular indexing and subsequent cDNA microarray analysis. FEBS Letters, Oct. 16, 2002, pp. 354-358, 531, Elsevier,Amsterdam, Netherlands.

Koh, W. et al., Noninvasive in vivo monitoring of tissue-specific global gene expression in humans, PNAS 111(20):7361-7366 (Jul. 29, 2014).

Krupp, et al. RNA-Seq Atlas—a reference database for gene expression profiling in normal tissue by next-generation sequencing. Bioinformatics. Apr. 15, 2012;28(8):1184-5.

Li, S. et al. Blood transcriptomics and metabolomics for personalized medicine. Computational and Structural Biotechnology Journal 14:1-7 (2016).

Li, S. et al. Molecular signatures of antibody responses derived from a systems biology study of five human vaccines. Nature Immunology, 15(2):195-204 (Feb. 2014).

Maron et al., Gene expression analysis in pregnant women and their infants identifies unique fetal biomarkers that circulate in maternal blood. The Journal of Clinical Investigation, Oct. 2007, 117(10), pp. 3007-3019.

Mitchell, et al. Circulating microRNAs as stable blood-based markers for cancer detection. Proc Natl Acad Sci USA 105 (2008): 10513-8.

Miura, et al. Identification of pregnancy-associated microRNAs in maternal plasma. Clin Chem. Nov. 2010;56(11):1767-71.

Miyamoto, et al. Detection of cell-free, liver-specific mRNAs in peripheral blood from rats with hepatotoxicity: a potential toxicological biomarker for safety evaluation. Toxicol Sci. Dec. 2008;106(2):538-45.

Pavlidis et al. Analysis of strain and regional variation in gene expression in mouse brain. Genome Biology, 2001, pp. 1-15, 2 (10).

PCT/US2018/051674 International Search Report and Written Opinion dated Jan. 18, 2019.

Porter, et al. A SAGE (serial analysis of gene expression) view of breast tumor progression. Cancer Res. 61(15):5697-702 (Aug. 1, 2001).

Redell, et al. Human traumatic brain injury alters plasma microRNA levels. J Neurotrauma. Dec. 2010;27(12):2147-56.

Savelyeva, Anna V et al. Vesicular and Extra-Vesicular RNAs of Human Blood Plasma. Advances in experimental medicine and biology vol. 924 (2016): 117-119.

Scherzer, C. R. Chipping away at diagnostics for neurodegenerative diseases. Neurobiology of Disease, Mar. 10, 2009, pp. 148-156, 35, Elsevier, Amsterdam, Netherlands.

Staal, et al. DNA microarrays for comparison of gene expression profiles between diagnosis and relapse in precursor-B acute lymphoblastic leukemia: choice of technique and purification influence the identification of potential diagnostic markers. Leukemia. Jul. 2003;17(7):1324-32.

Su, et al. A gene atlas of the mouse and human protein-encoding transcriptomes. Proc Natl Acad Sci USA, Apr. 20, 2004, pp. 6062-6067, 101 (16).

Urbanova, Marketa, et al. Circulating nucleic acids as a new diagnostic tool Cellular and Molecular Biology Letters, vol. 15, No. 2 (2010): 242-259.

U.S. Appl. No. 16/824,413 Office Action dated Jul. 21, 2021.

Baccarelli, Andrea et al. Ischemic heart disease and stroke in relation to blood DNA methylation. Epidemiology (Cambridge, Mass.) vol. 21,6 (2010): 819-28.

Cobb, J., et al. Sepsis gene expression profiling: murine splenic compared with hepatic responses determined by using complementary DNA microarrays. Critical care medicine 30.12 (2002): 2711-2721.

Co-pending U.S. Appl. No. 17/724,971, inventors Nerenberg; Michael et al., filed Apr. 20, 2022.

Co-pending U.S. Appl. No. 17/991,739, inventors Nerenberg; Michael et al., filed Nov. 21, 2022.

Fisher, C., et al. Hepatic Cytochrome P450 Enzyme Alterations in Humans with Progressive Stages of Nonalcoholic Fatty Liver Disease. Drug Metabolism and Disposition Oct. 1, 2009, 37 (10) 2087-2094.

Li, Huaping et al. Identification of cardiac-related circulating microRNA profile in human chronic heart failure. Oncotarget vol. 7,1 (2016): 33-45. doi:10.18632/oncotarget.6631.

Pirola, Carlos J. et al. Circulating microRNA signature in nonalcoholic fatty liver disease: from serum non-coding RNAs to liver histology and disease pathogenesis. Gut vol. 64,5 (2015): 800-12.

Schulte, Christian et al. Diagnostic and prognostic value of circulating microRNAs in heart failure with preserved and reduced ejection fraction. World journal of cardiology vol. 7,12 (2015): 843-60. doi:10.4330/wjc.v7.i12.843.

Sun, Kun et al. Plasma DNA tissue mapping by genome-wide methylation sequencing for noninvasive prenatal, cancer, and trans-

(56) References Cited

OTHER PUBLICATIONS plantation assessments. Proceedings of the National Academy of Sciences of the United States of America vol. 112,40 (2015): E5503-12.

Suzuki, S., et al. The major cytochrome P450 subtype activities in diet-induced nonalcoholic steatohepatitis mouse model. Endocrinol Metab Syndr 4 (2015): 190.

U.S. Appl. No. 16/832,449 Office Action dated Oct. 21, 2021.

Wang, Guo-Kun et al. Circulating microRNA: a novel potential biomarker for early diagnosis of acute myocardial infarction in humans. European heart journal vol. 31,6 (2010): 659-66. doi:10.1093/eurheartj/ehq013.

Wang, Shuo et al. HIF3A DNA Methylation Is Associated with Childhood Obesity and ALT PLOS ONE vol. 10, No. 12 (2015) pp. 1-9.

Weiland, Matthew et al. Small RNAs have a large impact Circulating microRNAs as biomarkers for human diseases. RNA biology vol. 9,6 (2012): 850-9.

Kitamoto, Takuya et al. Targeted-bisulfite Sequence Analysis of the Methylation of CpG Islands in Genes Encoding PNPLA3, SAMM50, and PARVB of Patients With Non-alcoholic Fatty Liver Disease. Journal of Hepatology 63(2):494-502 (2015).

Qin et al., A novel blood collection device stabilizes cell-free RNA in blood during sample shipping and storage. BMC Research Notes 6:380 (2013).

U.S. Appl. No. 17/991,739 Office Action dated May 9, 2024.

* cited by examiner

*FIG. 11A*
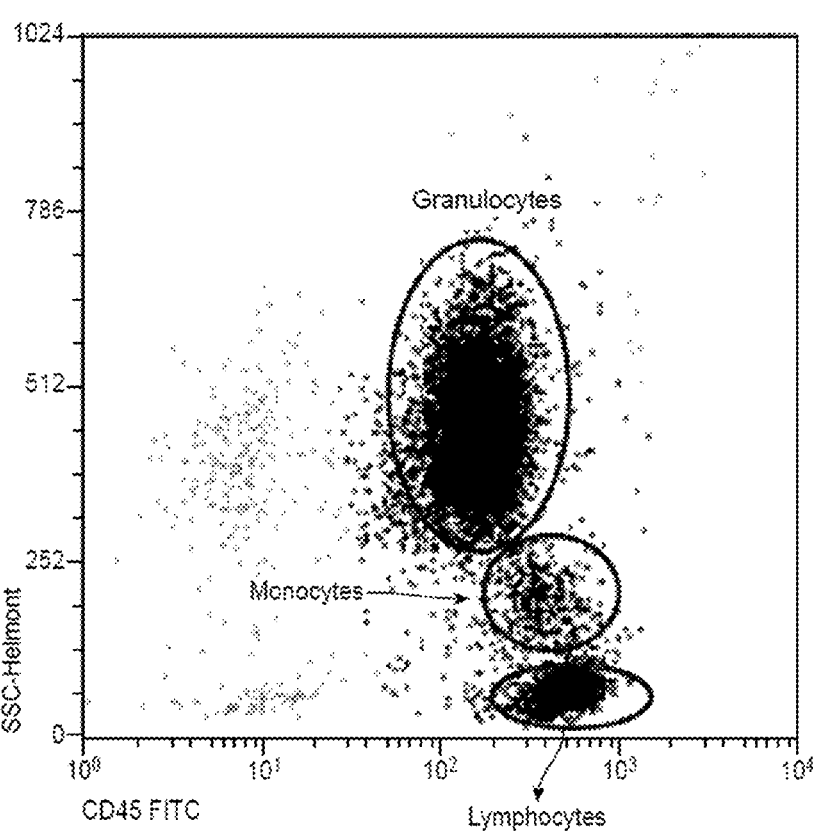
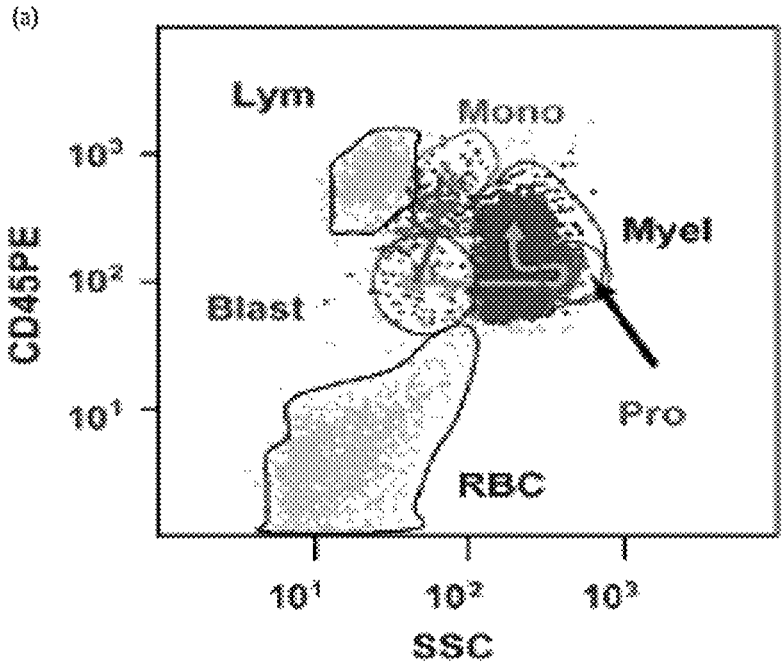
*FIG. 11B*

Side scatter b)

Granulocytes
Beads
Monocytes
Lymphocytes

CD45 PerCP

C04 A04
Gate: [No Gating]

SSC-A eos
1.0% gran
28.6% plat
28.6% mono
1.9% lymph
18.1%

CD45 PE-CY7-A

SEQUENCE LISTING

```
Sequence total quantity: 2
SEQ ID NO: 1            moltype = DNA   length = 22
FEATURE                 Location/Qualifiers
misc_feature            1..22
                        note = Description of Artificial Sequence:
                        Syntheticoligonucleotide
source                  1..22
                        mol_type = other DNA
                        organism = synthetic construct
SEQUENCE: 1
ggccctgtaa ttggaatgag tc                                          22

SEQ ID NO: 2            moltype = DNA   length = 21
```

-continued

```
FEATURE          Location/Qualifiers
misc_feature     1..21
                 note = Description of Artificial Sequence:
                 Syntheticoligonucleotide
source           1..21
                 mol_type = other DNA
                 organism = synthetic construct
SEQUENCE: 2
ccaagatcca actacgagct t                                                    21
```

METHODS AND SYSTEMS FOR DETECTING TISSUE CONDITIONS

CROSS-REFERENCE

This present application is a continuation of U.S. patent application Ser. No. 17/579,878, filed Jan. 20, 2022, which is a continuation of U.S. patent application Ser. No. 16/824, 413, filed on Mar. 19, 2020, which is a continuation application of International Patent Application Serial No. PCT/ US18/51674, filed on Sep. 19, 2018, which application claims the benefit of U.S. Provisional Patent Application Ser. No. 62/560,936 filed on Sep. 20, 2017, each of which is incorporated by reference herein in its entirety.

The instant application contains a Sequence Listing which has been submitted electronically in XML format and is hereby incorporated by reference in its entirety. Said XML copy, created on Aug. 29, 2022, is named 48198-705.303 SL.xml and is 3,708 bytes in size."

BACKGROUND OF THE INVENTION

A variety of markers are available for detecting various conditions. However, many of these conditions are ones that can affect different tissues. Detecting markers of these conditions in circulation, such as in a blood sample, are not always helpful in identifying which tissue is affected. For example, generic markers for inflammation can indicate an inflammatory response somewhere in the body, but it may not be known which tissue is suffering the response, such as the liver, kidney, lungs, or joints. Tissue-specific tests, such as biopsies, are often invasive, carrying a risk of infection, and typically not comprehensive of the entire organ or tissue. Imaging techniques, such as MRIs and CT-scans, may be used to assess tissue health, but generally can only detect overt features and changes. Thus, these imaging techniques are generally not sensitive enough to pick up early onset of conditions or fairly recent developments of conditions.

SUMMARY OF THE INVENTION

Disclosed herein, in some aspects, are methods comprising: obtaining a blood sample from a subject; removing cells from the blood sample to obtain a cell-depleted sample; removing an extracellular microparticle from the blood sample to obtain a microparticle-depleted sample; quantifying an amount of cell-free RNA corresponding to a gene in the microparticle-depleted sample. In some instances, removing the extracellular microparticle comprises contacting the cell-depleted sample with a binding moiety that interacts with a protein on the surface the extracellular microparticle. In some instances, the binding moiety is an antibody or antigen-binding antibody fragment. In some instances, the antibody or antigen-binding antibody fragment interacts with a cell surface marker known to be expressed by a blood cell. In some instances, the antibody comprises an anti-CD45 antibody. In some instances, the antibody comprises an anti-CD66b antibody. In some instances, methods comprise contacting the cell-depleted sample with a first antibody that interacts with a first protein on a first cell and a second antibody that interacts with a second protein on a second cell. In some instances, the first protein is not expressed on the second cell and the second protein is not expressed on the first cell. In some instances, the extracellular microparticle is an exosome. In some instances, the exosome is from a blood cell. In some instances, the blood cell is a platelet and wherein removing the extracellular microparticle comprises contacting the cell-depleted sample with an anti-GypA antibody or GypA antigen-binding fragment thereof. In some instances, the blood cell is a red blood cell and wherein removing the extracellular microparticle comprises contacting the cell-depleted sample with an anti-CD235a antibody or CD235a antigen-binding fragment thereof. In some instances, the blood cell is a granulocyte and wherein removing the extracellular microparticle comprises contacting the cell-depleted sample with an anti-CD66b antibody or CD66b antigen-binding fragment thereof. In some instances, the blood cell is a lymphocyte and wherein removing the extracellular microparticle comprises contacting the cell-depleted sample with an antibody or antigen-binding fragment thereof that binds CD45, CD19 or CD3. In some instances, the cell-depleted sample is incubated 1 h at 60 degrees Celsius. In some instances, methods comprise incubating the cell-depleted sample in the presence of a chaotropic salt, detergent, proteinase K, 2-mercaptoethanol, or a combination thereof. In some instances, methods comprise incubating the sample with Tris. In some instances, methods comprise disrupting lipidic and proteinaceous structures. In some instances, methods comprise contacting the cell-depleted sample with a silica column. In some instances, methods comprise incubating the cell-depleted sample with a chaotropic salt and 100% isopropanol to enhance the binding of RNA to the silica column.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 11A-D shows a CD45 binding moiety can capture multiple types of blood cells and extracellular microparticles thereof.

FIG. 12A shows sensitivity before improvements and FIG. 12B shows sensitivity after improvements.

DETAILED DESCRIPTION OF THE INVENTION

Figure 1:
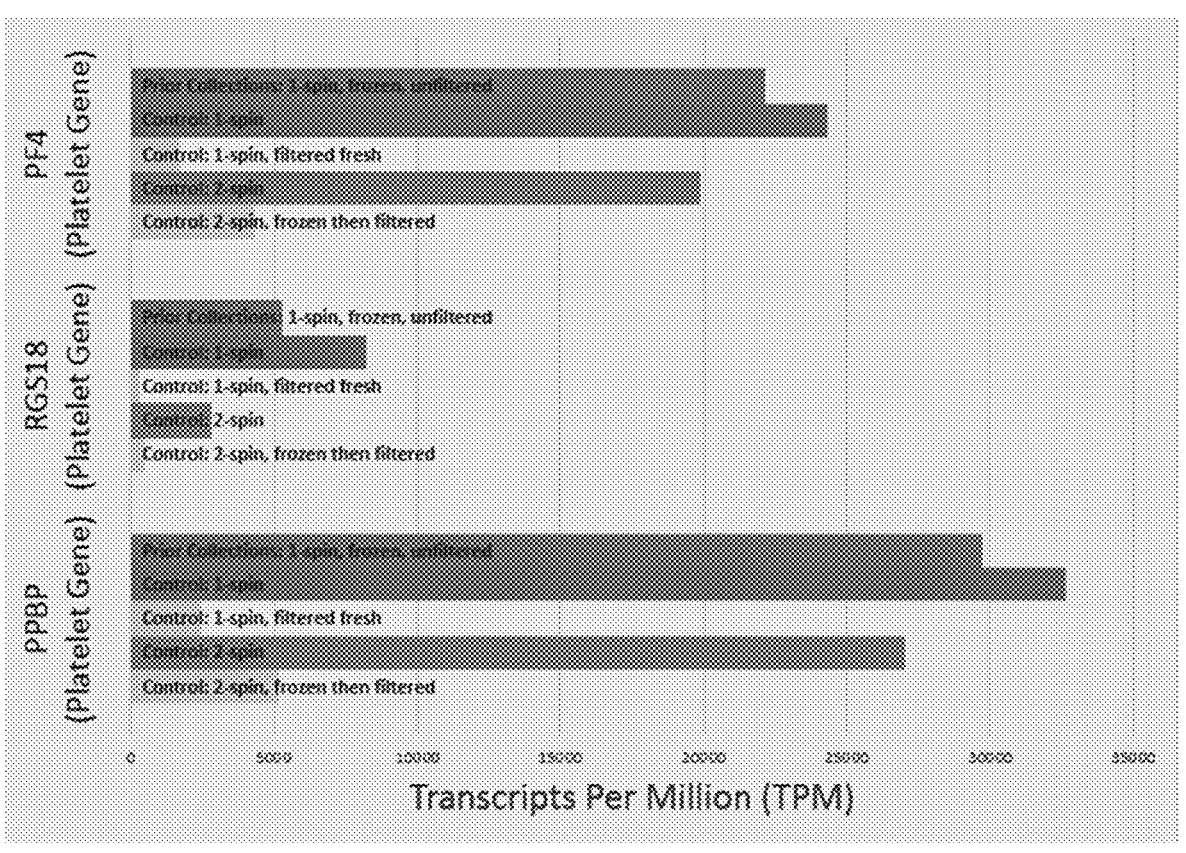
FIG. 1 shows freshly filtered samples have the least amount of blood cell contamination and are optimal for cell-free RNA studies.
Figure 2:
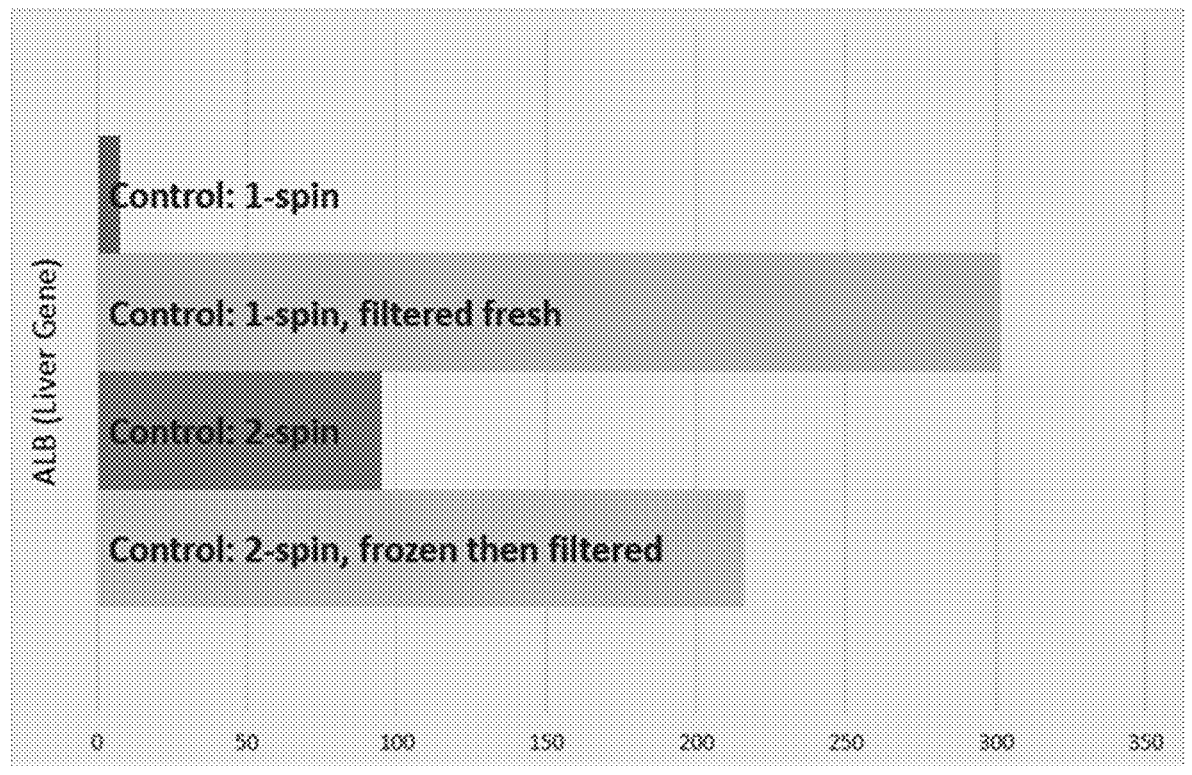
FIG. 2 shows the signal for non-blood cell transcripts (liver RNA) is two-fold higher after filtration of a blood sample.

One who aims to analyze RNA in blood from non-blood cells encounters a lot of unaligned RNA and very little informative mRNA. This can be improved by improving the extraction efficiency and amount from blood. This can be further improved by enrichment, i.e. using commercially available capture based kits prior to sequencing. At the end of this process, informative RNA (e.g. useful tissue specific mRNA from liver) is typically less than ~0.3%. This is a problem because, greater than 99.7% of sequencing is wasted on non-informative reads. The reason for this is that blood cell-encoded mRNAs constitute the majority of cell-free RNA in the blood. In typical poorly processed blood samples (e.g., using low speed centrifugation to get rid of cells), greater than 85% of the resulting plasma will be platelet transcripts. This can be reduced but not eliminated by high speed centrifugation (e.g. 16,000×g) or by filtration to remove large platelet and other cell fragments. The next most common contaminant is granulocyte transcripts, followed by mononuclear cell and RBCs. Unfortunately these cannot be removed simply by centrifugation and are likely contributed by exosomes produced by those cells. An attempt to remove these by high speed centrifugation, would likely remove most exosomes and greatly decrease organ specific signals.

An alternative is to selectively immunodeplete exosomes contributed by cells that are not of interest. This can be accomplished by using antibodies that are specific for the cells of origin. However, the exosomes have to express a high enough level of these antigens to allow immunodepletion. For example, the level of CD45 on exosomes from lymphocytes is high enough, while that on granulocytes is apparently not high enough as determined by plasma sequencing. The goal is to identify appropriate antibodies that will allow immunodepletion. A combination of CD41 (platelets), CD66b (granulocytes), CD235 (RBCs), CD45 (lymphocytes) antibodies may be used to remove these contaminating exosomes. This will allow one to process a much larger sample of plasma, and should make it a lot more efficient to pull out tissue-specific RNAs.

An alternative where we know exactly which tissue or which cell type we want to study (e.g. hepatocytes only) is to perform direct immunoenrichment rather than depletion. In this case we will use tissue specific Abs (e.g. ASGR1 for hepatocytes) to immunoenrich exosomes that are liver specific.

Methods, systems and kits described herein relate to the rapid, noninvasive detection of disorders using a combination of marker types so as to concurrently determine both a likely disorder and a likely tissue under duress. Through practice of the disclosure herein, one is able to make confident predictions as to a disease identity and the extent of its impact on one or more tissues, without requiring any invasive investigation of the tissue or tissues suspected of being impacted.

Often but not exclusively, one of the markers is circulating RNA that can be readily correlated to a tissue of origin, such that an increase in the relative contribution of RNA from that organ is indicative of duress in or specific to that organ. Single markers and aggregate RNA derived from an organ are both contemplated in various embodiments as indicators of tissue status. Alternately or in combination, circulating DNA, such as DNA that is differentially methylated in a tissue-specific manner, is included as part or all of a tissue-specific marker.

Concurrently, markers indicative of a type of disorder are also measured. There is a broad range of markers contemplated as indicative of a type disorder, including proteins, steroids, lipids, cholesterols, or nucleic acids such as DNA or RNA. RNA such as particular transcripts encoding proteins implicated in a disease or disorder are particularly useful, as are DNA having methylation patters that are indicative of a disease state. Often but not always, the disease marker is also a circulating marker that is readily obtained from, for example, a blood draw. However, alternatives such as X-ray, MRI or other data are contemplated as markers for some diseases.

By comparing the levels or identities of these markers to reference values or datasets, one may categorize a patient or a patient's sample as being indicative of a particular disease in the patient, localized as a particular tissue or organ. The reference values or datasets will vary as to the disease and tissue, and will variously include data from one or more healthy individuals, one or more individuals suffering from various extents of a disorder or tissue duress, data from intermediate individuals, and data predicted from models. A sample can be categorized as indicative of a disorder or condition when its values are individually or collectively above or below a threshold, or when they do not differ significantly from a reference data set correlated with the disorder or condition, or when they do differ significantly from a reference dataset correlated with absence of the disease or disorder.

For instance, methods, systems and kits described herein may be used to screen for development or progression of a condition, or multiple conditions, in multiple organs, in an at-risk population on a routine basis. This can be especially useful in subjects with chronic conditions, such as metabolic syndrome, obesity, diabetes, neurodegenerative disorders and cancer, where one or more tissues are at risk of injury, damage or failure.

Metabolic syndrome and obesity affect a large and ever-growing percentage of the population worldwide. This population is at a constant and relatively high risk of developing life-threatening complications, such as heart attack, stroke, liver cirrhosis, pancreatic exhaustion, and kidney failure. Thus, this population is at a constant risk of developing complications in an array of organs and tissues. Similarly, many cancers are at a constant risk of mutating and metastasizing to different tissues and organs. In addition, treatments for cancer are often administered with uncertainty of success, and it is desirable to rapidly determine whether or not these treatments are effective or toxic. In these exemplary cases, it is not practical to assess subjects on a routine basis using traditional methods, such as imaging techniques and biopsies. However, methods, systems and kits, such as those described herein, provide for rapidly detecting insult, increased risk and therapeutic effects in one or more organs in a subject, thereby providing a means to monitor subjects with chronic conditions for acute complications, disease progression, and therapeutic effects.

The following methods, kits, and systems are intended to rapidly and non-invasively detect tissues or organs in a subject that are under duress, damaged or affected by a condition or disease. In some instances, the following methods, kits, and systems also determine which disease or condition is affecting the tissue under duress or to what extent the disease or condition is affecting the tissue. A sample, such as blood plasma, saliva, or urine, is collected from the subject and analyzed for markers and cell-free polynucleotides that can indicate disease and disease location in the subject. These methods, kits and systems generally rely on circulating, cell-free nucleic acids that are released or secreted from the tissue or organ under duress into biological fluids, such as cell-free RNA in a plasma or urine sample. By focusing on genes that are specifically expressed or predominantly expressed in a certain tissue, inferences or conclusions can be drawn about the health status of that tissue based on the relative contribution of RNA from the tissues to total circulating RNA. By quantifying relative contributions, one can advantageously locate tissues affected by a condition without invasive biopsies or macroscale-limited imaging techniques. Tissue-specific nucleic acids are used in combination with markers for various conditions to select therapies, monitor effects of therapies, and monitor progression of a disease or condition.

Identifying diseases and tissues under duress may require comparing levels of tissue-specific polynucleotides and markers in a sample of a test subject to those of at least one sample from a control subject. The tissue-specific polynucleotides and markers may be referred to as a panel herein. In some instances, levels of markers and tissue-specific polynucleotides in a sample that is obtained from a test subject are compared to those of a control subject. In some instances, levels of markers and tissue-specific polynucleotides in a sample that is obtained from a test subject are compared to an average of corresponding levels in multiple control subjects. The control subjects may have a condition of interest or the control subjects may be subjects without the condition.

Methods, systems and kits provide for detecting or quantifying a panel of tissue-specific polynucleotides and/or markers. It is recognized that gene expression may vary tremendously within a population of subjects and between populations of subjects (e.g., between different ethnic groups), and in such cases, a panel of tissue-specific polynucleotides and/or markers may be particularly useful. For instance, the methods may comprise comparing the panel to at least one control panel. While the expression levels of each tissue-specific polynucleotide and marker may not be similar, a conclusion or inference can still be made about the condition or tissue(s) of the subject if the panel is sufficiently similar or sufficiently different from a control panel. In this way a panel may provide an advantage over using a single marker of disease or a single tissue-specific polynucleotide. In some instances, the methods comprise comparing the panel of a subject at a first time point to the panel of the subject at a second time point. Thus, a single subject's natural genetic variations and gene expression fluctuations are controlled for and differences between panels are more likely due to changes in the condition or tissue(s) affected. In some instances, the panel may comprise non-polynucleotide molecules. The panel may comprise polynucleotides and other biological molecules (e.g., peptides, lipids, pathogen fragments, etc.).

Methods, kits, and systems described herein may be used to determine the likelihood or risk of the subject developing the disease or condition, the progression or severity of the disease or condition, or the effect of a therapy or treatment on the disease or condition. Kits, systems and methods disclosed herein are sensitive and accurate enough to compare a first level of a marker or tissue-specific polynucleotide to a second level of the marker or tissue-specific nucleic acid, in order to differentiate between a risk of a condition, a progressed state of a condition, or an improvement of a condition by a treatment. In some instances, the first level of the marker or tissue-specific nucleic acid corresponds to a sample from a subject at a first time point and the second level of the marker or tissue-specific nucleic acid corresponds to a second sample from a subject at a second time point.

Multiple diseases and tissues may be assessed simultaneously using the kits, systems and methods disclosed herein. In this way, the kits, systems and methods disclosed herein may be used to assess the presence or absence of at least one condition and identify both affected and unaffected tissues. In some embodiments, methods comprise selecting or recommending a medical action based on results produced by the methods, systems or kits disclosed herein. In some embodiments, a customized medical action is recommended, and optionally taken, based on the determination. In some instances, customized medical action comprises directly treating a tissue under duress, e.g., with radiation or injection of the tissue. Non-limiting examples of medical actions include performing additional tests (e.g., biopsy, imaging, surgery), treating the subject for the disease or condition, and modifying a treatment of the subject (e.g. altering the dose of a pharmaceutical composition, ceasing administration of a pharmaceutical composition, administering a different or additional pharmaceutical composition).

The systems, methods and kits disclosed herein may provide for detecting a condition or disease in multiple tissues. In some instances, a subject has a condition known to affect one or more tissues depending on the extent or severity of the condition. Systems, methods and kits, such as those disclosed herein, advantageously allow for identification and targeted treatment of multiple tissues under duress. For example, a system disclosed herein may provide markers for detecting inflammation in a subject and determining that the liver and heart are affected by the inflammation due to the levels of circulating liver-specific RNAs and heart-specific RNAs. Also, by way of example, the methods may comprise detecting cell-free RNA in a plasma sample that harbor mutations associated with cancer (e.g., mutations that occur as a cause or consequence of cancer), or that is present at a level indicative of cancer. Once the presence of a cancer is detected, the methods may further comprise quantifying tissue-specific, relative contributions cell-free RNAs from various tissues to determine which tissues may be harboring a tumor, or beginnings thereof.

In addition to detecting tissues that are damaged, the methods further provide for identifying, or differentiating between, conditions that are causing the tissue damage. By way of non-limiting example, methods are disclosed herein for detecting liver damage in a subject, identifying a condition causing the liver damage, selecting a therapy to treat the subject and monitoring the effectiveness of the therapy. Cell-free RNA that corresponds to genes predominantly expressed in the human liver is quantified in a plasma sample of a subject. Elevated levels of such RNA in the plasma sample indicate there is liver damage. Identifying, or differentiating between, diseases, as described herein, generally depends on quantifying, not merely detecting, the tissue-specific RNA and quantifying markers of disease. For example, non-alcoholic fatty liver disease (NAFLD) and the more progressed and severe disease, non-alcoholic steatohepatitis (NASH) may be identified by similar liver-specific RNA and markers, but levels of these molecules may be higher in cases of NASH than in cases of NAFLD because there is more liver damage occurring in NASH than NAFLD. Since more damage of the liver occurs in NASH than NAFLD in most cases, more liver-specific RNA will be released from the liver in a case of NASH than in a case of NAFLD.

Disease presence and location in a subject can be determined at an early stage of disease, because the systems and methods described herein provide rapid results, are non-invasive and inexpensive. Thus, the subject can be advantageously treated before the disease progresses to advanced stages that are relatively more difficult to control or treat as compared to early stages. For example, the systems and methods disclosed herein may allow for determining which tissue(s) or organ(s) have cancerous cells before a tumor is large enough to be visualized with an imaging technique, such as a CT or PET scan. In this way, the methods and systems disclosed herein provide for focused analysis and targeted therapies, such as local injection and targeted radiation, at early stages of disease.

Advantageously, the methods and systems provide for treating with a therapy that is suitable or optimal for the extent of tissue damage. In some instances, the methods comprise detecting/quantifying the markers and/or tissue-specific polynucleotides to assess the effectiveness or toxicity of a therapy. In some instances the therapy is continued. In other instances, the therapy is discontinued and/or replaced with another therapy. Regardless, due to the rapid and non-invasive nature of the methods and systems, therapeutic effects can be assessed and optimized more often relative to conventional treatment optimization.

By way of non-limiting example, according to conventional practice, a patient being treated for cancer is administered a chemotherapy and an MRI is performed three months later to determine if tumor size is reduced. When an increase in tumor size is observed, the medical practitioner prescribes a different therapy, but the tumor has already metastasized. In contrast, using methods described herein, the patient would be tested one to two weeks after initiating treatment to assess levels of tissue-specific nucleic acids corresponding to tissues harboring tumors as well as markers of treatment effectiveness. When levels of tissue-specific nucleic acids and markers indicate the therapy is ineffective, the practitioner prescribes a different therapy that is quickly determined, by similar methods, to be effective. In the latter case, tumors have less time to grow relative to the conventional method that utilizes imaging techniques and do not metastasize, thereby providing the patient with a better prognosis.

In some aspects, the present disclosure provides for uses of systems, samples, markers, and tissue-specific polynucleotides disclosed herein. In some instances, disclosed herein are uses of an in vitro sample for non-invasively detecting a tissue or organ in a subject that is under duress and as well as a disease or condition that is the cause of the duress. In some instances, disclosed herein are uses of an ex vivo sample for non-invasively detecting a tissue or organ in a subject that is under duress and as well as a disease or condition that is the cause of the duress. Generally, uses disclosed herein comprise quantifying markers and tissue-specific polynucleotides in samples, including ex vivo samples and in vitro samples. Some uses disclosed herein comprise comparing a quantity of a marker and a quantity of tissue-specific polynucleotide in a first sample and comparing the quantities to respective quantities in a second sample. In some instances, the first sample is from a first subject and the second sample is from a control subject (e.g., a healthy subject or subject with a condition). In some instances, the first sample is from a subject at a first time point and the second sample is from the same subject at a second time point. The first time point may be obtained before the subject is administered a therapy and the second time point may be obtained after the therapy. Thus, also provided herein are uses of samples, markers, tissue-specific polynucleotides, kits and systems disclosed herein to monitor or evaluate a condition of a subject, tissue health state of a subject, or an effect of a therapeutic agent.

Certain Terminologies

The following descriptions are provided to aid the understanding of the methods, systems and kits disclosed herein. The following descriptions of terms used herein are not intended to be limiting definitions of these terms. These terms are further described and exemplified throughout the present application.

Methods, systems and kits described herein generally detect and quantify cell-free nucleic acids. For this reason, biological samples described herein are generally acellular biological fluids. Samples from subjects, by way of non-limiting example, may be blood from which cells are removed, plasma, serum, urine, or spinal fluid. For instance, the biological molecule may be circulating in the bloodstream of the subject, and therefore the detection reagent may be used to detect or quantify the marker in a blood or serum sample from the subject. The terms "plasma" and "serum" are used interchangeably herein, unless otherwise noted. However, in some cases they are included in a single list of sample species to indicate that both are covered by the description or claim.

The term "tissue-specific polynucleotide," e.g., "tissue-specific RNA," as described herein generally refers to a polynucleotide that is predominantly expressed in a specific tissue. Often, methods, systems and kits disclosed herein utilize cell-free, tissue-specific polynucleotides. Cell-free, tissue-specific polynucleotides described herein are polynucleotides expressed at levels that can be quantified in a biological fluid upon damage of the tissue or organ in which they are expressed. In some cases, the presence of cell-free tissue-specific polynucleotides disclosed herein in a biological fluid is due to release of cell-free tissue-specific polynucleotides upon damage of the tissue or organ, and not due to a change in expression of the cell-free tissue-specific polynucleotides. Elevated levels of cell-free tissue-specific polynucleotides disclosed herein are indicative of damage to the corresponding tissue or organ. In some instances, cell-free polynucleotides disclosed herein are expressed/produced in several tissues, but at tissue-specific levels in at least one of those tissues. In these cases, the absolute or relative quantity of the cell-free tissue-specific polynucleotide is indicative of damage to a specific tissue or organ, or collection of tissues or organs. Alternatively or additionally, tissue-specific polynucleotides are nucleic acids with tissue-specific modifications. By way of non-limiting example, tissue-specific polynucleotides or markers disclosed herein include DNA molecules (e.g., a portion of a gene or non-coding region) with tissue-specific methylation patterns. In other words, the polynucleotides and markers may be expressed similarly in many tissues, or even ubiquitously throughout a subject, but the modifications are tissue-specific. Generally, tissue-specific polynucleotides or levels thereof disclosed herein are not specific to a disease. Generally, tissue-specific polynucleotides disclosed herein do not encode a protein implicated in a disease mechanism.

The term, "marker," as used herein, encompasses a wide variety of biological molecules. Markers may also be referred to herein as disease markers or markers of disease. In some instances, the marker is for a condition associated with a plurality of diseases. For example, the marker may be for inflammation, which can be associated with cardiovascular disease, hepatitis and cancer. Markers, by way of non-limiting example, include peptides, hormones, lipids, vitamins, pathogens, cell fragments, metabolites and nucleic acids. In some instances, a marker is a cell-free nucleic acid. Generally, markers disclosed herein are not tissue-specific. However, in rare instances, the markers are tissue-specific. Markers disclosed herein may also be referred to as disease biomarkers. The disease biomarker is a biological molecule that is present or produced as a result of a disease, dysregulated as a result of a disease, mechanistically implicated in a disease, mutated or modified in a disease state, or any combination thereof. Markers may be produced by the subject. Markers may also be produced by other species. For instance, the marker may be a nucleic acid or protein made by a hepatitis virus or a *Streptococcus* bacterium. Methods identifying such markers may further comprise detecting/quantifying tissue-specific polynucleotides to determine which tissues are infected or affected by these pathogens, and optionally, to an extent that the tissue(s) are damaged. Markers of diseases disclosed herein generally do not circulate in individuals unaffected by the disease.

In general, the terms "cell free polynucleotide," and "cell free nucleic acid," used interchangeably herein, refers to a polynucleotide that can be isolated from a sample without extracting the polynucleotide from a cell. Cell free polynucleotides disclosed herein are typically polynucleotides that have been released or secreted from a damaged tissue or damaged organ. For example, damage to the tissue or organ may be due to a disease, injury or other condition that resulted in cytolysis, releasing the cell-free polynucleotide from cells of the damaged tissue into circulation. In some instances, a cell free polynucleotide disclosed herein is tissue-specific. In other instances, a cell free polynucleotide is not tissue-specific. In some instances, a cell free polynucleotide is present in a cell or in contact with a cell. In some instances, a cell free polynucleotide is in contact with an organelle, vesicle or exosome. In some instances, a cell free polynucleotide is cell-free, meaning the cell free polynucleotide is not in contact with a cell. Cell-free polynucleotides described herein are freely circulating, unless otherwise specified. In some instances, a cell free polynucleotide is freely circulating, that is the cell free polynucleotide is not in contact with any vesicle, organelle or cell. In some instances, a cell free polynucleotide is associated with a polynucleotide-binding protein (transferases, ribosomal proteins, etc.), but not any other molecules.

As used herein, the term 'about' a number refers to that number plus or minus 10% of that number. The term 'about' a range refers to that range minus 10% of its lowest value and plus 10% of its greatest value.

As used in the specification and claims, the singular forms "a", "an" and "the" include plural references unless the context clearly dictates otherwise. For example, the term "a sample" includes a plurality of samples, including mixtures thereof.

The terms "determining", "measuring", "evaluating", "assessing," "assaying," and "analyzing" are often used interchangeably herein to refer to forms of measurement, and include determining if an element is present or not (for example, detection). These terms can include quantitative, qualitative or quantitative and qualitative determinations. Assessing is alternatively relative or absolute. "Detecting the presence of" includes determining the amount of something present, as well as determining whether it is present or absent.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

Methods

As discussed in the foregoing and following description, methods disclosed herein are intended to non-invasively detect a tissue or organ in a subject that is under duress as well as determine which disease or condition is affecting the tissue or organ under duress. Some methods disclosed herein comprise determining a stage or progress of a disease or condition in a subject. Some methods disclosed herein comprise determining a response to a therapy used to treat a disease or condition in a subject. Some methods disclosed herein comprise determining if a particular tissue or organ in a subject is damaged, injured or infected. Some methods disclosed herein comprise determining if a particular tissue or organ in a subject is affected by a disease or condition. Some methods disclosed herein comprise detecting or quantifying a biological molecule disclosed herein. Some methods disclosed herein comprise detecting or quantifying a marker and/or tissue-specific polynucleotide disclosed herein.

Some methods disclosed herein comprise detecting, quantifying and/or analyzing at least one nucleic acid in a sample of the subject. The methods may comprise detecting, quantifying, and/or analyzing at least one nucleic acid in a biological sample. In some instances, the biological sample has been frozen. In some instances, the biological sample has never been frozen. The tissue-specific polynucleotide may be a tissue-specific, cell-free polynucleotides. The methods may further comprise comparing the quantity of the marker and/or the tissue-specific, cell-free polynucleotide to a reference level of the marker and a reference level of the tissue-specific polynucleotide, respectively. In some instances, comparison to a reference level is not required. For example, the presence of the marker and/or tissue-specific, cell-free polynucleotide may be sufficient to detect the disease or condition, or determine if the particular tissue is damaged, injured or infected by the disease or condition. In some aspects, the methods provide for the diagnosis or prognosis of the disease or condition, or assessing the progression thereof.

In some aspects, the present disclosure provides for methods of enriching for circulating non-blood RNA in a blood sample, comprising depleting the blood sample of blood cells; and depleting the blood sample of exosomes. In some aspects, the present disclosure provides for methods of enriching for circulating non-blood RNA in a blood sample, comprising depleting the blood sample of blood cells to produce a cell-depleted blood sample; and contacting the cell-depleted blood sample with a blood cell surface binding moiety.

In some aspects, the present disclosure provides for methods comprising: (a) obtaining a blood sample from a subject; (b) removing cells from the blood sample to obtain a cell-depleted sample; (c) removing an extracellular microparticle from the blood sample to obtain a microparticle-depleted sample; and (d) quantifying an amount of RNA corresponding to a gene in the microparticle-depleted sample. In some instances, the methods comprise: (a) obtaining a blood sample from a subject; (b) centrifuging or filtering the blood sample to obtain a plasma sample; (c) filtering the plasma sample to remove platelets from the plasma sample, thereby producing a cell-depleted sample; (d) contacting the cell-depleted sample with a cell-surface protein binding moiety, wherein the cell-surface protein binding moiety is capable of binding a cell-surface protein on a blood-cell exosome in the cell-depleted sample; (e) removing the cell-surface protein binding moiety from the cell-depleted sample, thereby removing the blood-cell exosome from the cell-depleted sample; and (f) quantifying circulating cell-free RNA in the cell-depleted sample, wherein the cell-free RNA is expressed by a tissue of interest.

Removing Cells

In some aspects, the present disclosure provides for methods that comprise removing a cell from a sample disclosed herein (e.g., biological fluid, blood, plasma sample, cell-depleted sample). In some instances, removing the cell comprises centrifuging the sample. In some instances, removing the cell comprises centrifuging the sample more than once. In some instances, removing the cell comprises centrifuging the sample twice. In some instances, methods comprise centrifuging the sample at about 5,000 g to about 25,000 g. In some instances, methods comprise centrifuging the sample at about 8,000 g to about 20,000 g. In some instances, methods comprise centrifuging the sample at about 12,000 g to about 18,000 g. In some instances, methods comprise centrifuging the sample at about 14,000 g to about 18,000 g. In some instances, methods comprise centrifuging the sample at about 16,000 g. In some instances, removing the cell comprises filtering the sample. Filtering the sample may comprise contacting the sample with filter having a pore diameter of about 200 micron to about 1000 micron. Filtering the sample may comprise contacting the sample with an 800 micron filter.

In some aspects, the present disclosure provides for methods that comprise removing a cell from a sample disclosed herein to produce a cell-depleted sample as described herein. In some instances, the cell-depleted sample is substantially free of cells. In some instances, the cell-depleted sample contains less than about 10 cells. In some instances, the cell-depleted sample contains less than about 50 cells. In some instances, the cell-depleted sample contains less than about 100 cells. In some instances, the cell-depleted sample contains less than about 150 cells. In some instances, the cell-depleted sample contains less than about 200 cells. In some instances, the cell-depleted sample contains less than about 500 cells. In some instances, the cell-depleted sample contains less than about 1000 cells.

In some instances, the cell is a blood cell. In some instances, the cell is a leukocyte. In some instances, the cell is selected from a T cell, a B cell, a dendritic cell, a natural killer cell, a stem cell precursor, a macrophage, a monocyte, a granulocyte, a platelet, an erythrocyte, a circulating endothelial cell, or a circulating epithelial cell. In some instances, the cell is a platelet. In some instances, the cell is a granulocyte.

Some methods disclosed herein comprise removing at least about 90% of the cells that were originally present in the blood sample. Some methods disclosed herein comprise removing at least about 95% of the cells that were originally present in the blood sample. Some methods disclosed herein comprise removing at least about 75% to at least about 95% of the cells that were originally present in the blood sample. Some methods disclosed herein comprise removing at least about 75% to at least about 99% of the cells that were originally present in the blood sample. In some instances, the cells include cell fragments in the sample. Such samples may be referred to herein as a "cell-depleted sample."

Removing Extracellular Microparticles

In some aspects, the present disclosure provides for methods that comprise removing an extracellular microparticle from a sample disclosed herein (e.g., biological fluid, blood, plasma sample, cell-depleted sample). In some aspects, the present disclosure provides for methods that comprise removing at least one extracellular microparticle from a sample. In some aspects, the present disclosure provides for methods that comprise removing a plurality of extracellular microparticles from a sample. In some instances, the extracellular microparticle is characterized as or referred to as an exosome, a vesicle, a microvesicle, an exosome-like vesicle, or a microparticle. In some instances, the extracellular microparticle is an exosome. In some instances, the extracellular particle is from a leukocyte. In some instances, the extracellular particle is from a blood cell. In some instances, the extracellular particle is from a circulating cell. More than 90% of exosomes in plasma or serum are from blood cells. Methods disclosed herein remove such extracellular microparticles, thereby improving the accuracy and sensitivity of circulating cell-free nucleic acid quantification.

Some methods comprise contacting the sample with a binding moiety that interacts with a protein on the surface the extracellular microparticle. In some instances, the sample is a cell-depleted sample. In some instances, the binding moiety interacts with a cell surface marker known to be expressed by a circulating cell. In some instances, the circulating cell is a bone marrow derived cell. In some instances, the circulating cell is a blood cell. In some instances, the circulating cell is a leukocyte. In some instances, the circulating cell is a T cell. In some instances, the circulating cell is a B cell. In some instances, the circulating cell is a dendritic cell. In some instances, the circulating cell is a natural killer cell. In some instances, the circulating cell is a stem cell precursor. In some instances, the circulating cell is a macrophage. In some instances, the circulating cell is a monocyte. In some instances, the circulating cell is a granulocyte. In some instances, the circulating cell is a platelet. In some instances, the circulating cell is an erythrocyte. In some instances, the circulating cell is a circulating endothelial cell. In some instances, the circulating cell is a circulating epithelial cell.

Some methods comprise contacting the sample with a binding moiety that interacts with a protein on the surface the extracellular microparticle. In some instances, the binding moiety is a receptor or a ligand for the protein on the surface of the extracellular microparticle. In some instances, the binding moiety is a binding protein. In some instances, the binding moiety is a small molecule. In some instances, the binding moiety is an aptamer or nucleic acid. In some instances, the binding moiety is a lipid, fatty acid, sterol or other biopolymer. In some instances, the binding moiety is an antibody. In some instances, the binding moiety is antigen-binding antibody fragment. In some instances, the antibody or antigen binding fragment thereof binds a cell surface marker selected from GypA, CD3, CD4, CD8, CD14, CD19, CD20, CD11c, CD123, CD56, CD34, CD14, CD33, CD66b, CD41, CD42b, CD61, CD62, CD138, CD235a, CD146 or CD326. In some instances, the extracellular microparticle is from a leukocyte and the cell surface marker is CD45. In some instances, the extracellular microparticle is from a granulocyte and the cell surface marker is CD66b.

Some methods comprise contacting the sample with a binding moiety that interacts with a protein on the surface the extracellular microparticle. In some instances, the binding moiety is attached to a solid support. In some instances, the binding moiety is connected to a solid support. In some instances, the binding moiety is conjugated to a solid support. In some instances, the binding moiety interacts with a solid support. Non-limiting examples of a solid support are a bead, a column, a plate, or an array. In some instances, the binding moiety has an affinity for a solution that is immiscible with the sample, such that when the solution is added to the sample after contacting the sample with the binding moiety, the binding moiety separates into the solution, thereby removing the extracellular particle from the sample.

Some methods comprise contacting the sample with a plurality of binding moieties that interacts with a plurality of proteins on the surface a plurality of extracellular microparticles. In some instances, methods comprise contacting the sample with at least two binding moieties. In some instances, methods comprise contacting the sample with at least three binding moieties. In some instances, methods comprise contacting the sample with at least four binding moieties. In some instances, methods comprise contacting the sample with about two binding moieties to about five binding moieties. Some methods comprise contacting the sample with a first binding moiety and a second binding moiety. In some instances, the first binding moiety interacts with a first protein on a first cell and a second antibody interacts with a second protein on a second cell. In some instances the first binding moiety and the second binding moiety are different. In some instances, the first protein and the second protein are the same. For instance, in some cases, the first binding moiety and the second binding moiety target the same protein, but both are used, because there is uncertainty about which binding moiety will work best in the subject's sample. In some instances, the first protein and the second protein are different. In some instances, the first protein and the second protein are different by at least about 10 amino acids. In some instances, the first protein and the second protein are different by at least about 100 amino acids. In some instances, the first protein and the second protein are different by at least about 200 amino acids. In some instances, the first protein and the second protein are different by at least about 400 amino acids. In some instances, the first protein and the second protein are expressed from different genes. In some instances, the first protein is not expressed on the second cell and the second protein is not expressed on the first cell. In some instances, the first cell and the second cell are two different types of leukocytes. In some instances, methods comprise removing cell fragments in a manner that is similar to removing extracellular microparticles, as disclosed herein.

Some methods disclosed herein comprise removing an extracellular microparticle from a sample disclosed herein. In some instances, the method depletes the blood sample of at least 90% of extracellular microparticles that were originally present in the blood sample. In some instances, the method depletes the blood sample of at least 99% of extracellular microparticles that were originally present in the blood sample.

Some method disclosed herein comprise removing additional components of the sample beyond cells, cell fragments, and extracellular microparticles. Non-limiting example of additional components are microRNA, ribosomal RNA, and tRNA, etc.

Capturing Extracellular Microparticles

In some aspects, the present disclosure provides for methods that comprise contacting a sample with a protein binding moiety, wherein the protein binding moiety is capable of binding a surface protein on an extracellular microparticle in the plasma sample, wherein the extracellular microparticle is from a tissue of the subject; removing the protein binding moiety from the cell-depleted sample, thereby removing the extracellular microparticle from the sample; and quantifying a nucleic acid in the extracellular microparticle, wherein the nucleic acid is expressed by the tissue. In some instances, the tissue of interest is not blood. In some instances, the tissue of interest is a solid organ. In some instances, the tissue of interest is liver, and the protein binding moiety interacts with SLC7A10 or fatty acid binding protein 4 (FABP4). In some instances, the tissue of interest is adipose, and the protein binding moiety interacts with asialoglycoprotein receptor 1 (ASGR1), or glial fibrillary acidic protein (GFAP). In some instances, the tissue of interest is neurological tissue, and the protein binding moiety interacts with glutamate aspartate transporter (GLAST). In some instances, the tissue of interest is kidney, and the protein binding moiety interacts with gamma-glutamyl-transpeptidase. In some instances, the cell-surface protein binding moiety is an antibody or antigen-binding fragment thereof. In some instances, the extracellular microparticle is an exosome. Non-limiting example of an exosome from a tissue or tumor includes a prostasome, an epididimosome, a dexosome, a texosome, and an oncosome.

Quantifying Nucleic Acids

In some aspects, the present disclosure provides for methods comprising quantifying RNA in a sample of a subject. In some instances, the sample is altered or processed as described herein. In some instances, the RNA is cell free RNA, which can also be referred to as circulating cell free RNA. In some instances, the RNA is not attached to a cell, a cell fragment, an extracelluar microparticle (e.g., exosome), or a fragment thereof. In some instances, the RNA comprises messenger RNA (mRNA). In some instances, the RNA consists essentially of mRNA. In some instances, the RNA is mRNA. In some instances, the RNA has a length of about 75 nucleotides to about 300 nucleotides. In some instances, the RNA has a length of about 100 nucleotides to about 250 nucleotides. In some instances, the RNA has a length of about 125 nucleotides to about 225 nucleotides. In some instances, the RNA has a length of about 300 nucleotides to about 5000 nucleotides.

Some methods comprise quantifying a relative contribution of the RNA to the sample. Some methods comprise quantifying a fraction of the RNA in the total RNA of the sample. Some methods disclosed herein comprise sequencing the RNA. In some instances, quantifying comprises Q-PCR. In some instances, quantifying comprises multiplexed PCR. In some instances, quantifying comprises an array detection method (e.g., microarray). In some instances, quantifying comprises random priming with simultaneous addition of adapters by priming and template-switching processes.

In some aspects, the present disclosure provides for methods comprising quantifying RNA in a sample of a subject. In some instances, the RNA is from a tissue. In some instances, the tissue is not a fluid tissue (e.g., blood). In some instances, the tissue is a solid tissue. In some instances, the tissue is an organ. In some instances, the tissue is associated with a function. For instance, the tissue may be a neurological tissue. Neurological tissue may be brain, spinal cord, peripheral nerves, or a combination thereof. Non-limiting example of tissues include liver, adipose, kidney. In some instances, the RNA is from a tissue-specific cell type. In some instances the tissue-specific cell type is a non-blood cell. In some instances, the tissue-specific cell type is a neurological cell type. Non-limiting examples of neurological cell types are astrocytes and oligodendrocytes. In some instances, the tissue-specific cell type is a hepatocellular type. Non-limiting examples of hepatocellular types are hepatocytes, Kuppfer cells, and stellate cells. In some instances, the tissue-specific cell type is a renal cell type. A non-limiting example of a renal cell type is a renal tubular cell.

In some aspects, the present disclosure provides for methods comprising quantifying RNA in a sample of a subject. In some instances, the RNA is more highly expressed in a tissue of interest than it is expressed in blood. In some instances, the RNA is more highly expressed in a tissue of interest than it is expressed in a blood cell. In some instances, the RNA is not expressed by a blood cell. In some instances, the RNA is expressed at least five fold higher in the tissue than in the blood. In some instances, the RNA is expressed at least ten fold higher in the tissue than in the blood. In some instances, the RNA is expressed at least twenty fold higher in the tissue than in the blood.

In some instances, the RNA is expressed at least five fold higher in the tissue than any other tissue. In some instances, the RNA is expressed at least ten fold higher in the tissue than any other tissue. In some instances, the RNA is expressed at least twenty fold higher in the tissue than any other tissue. In some instances, the RNA is expressed at least five fold higher in no more than two tissues than any other tissue. In some instances, the RNA is expressed at least ten fold higher in no more than two tissues than any other tissue. In some instances, the RNA is expressed at least twenty fold higher in no more than two tissues than any other tissue. In some instances, the RNA is expressed at least five fold higher in no more than three tissues than any other tissue. In some instances, the RNA is expressed at least ten fold higher in no more than three tissues than any other tissue. In some instances, the RNA is expressed at least twenty fold higher in no more than three tissues than any other tissue.

In some instances, the RNA is expressed at least five fold higher in a cell type than any other cell type. In some instances, the RNA is expressed at least ten fold higher in the cell type than any other cell type. In some instances, the RNA is expressed at least twenty fold higher in the cell type than any other cell type. In some instances, the RNA is expressed at least five fold higher in no more than two cell types than any other cell types. In some instances, the RNA is expressed at least ten fold higher in no more than two cell types than any other cell types. In some instances, the RNA is expressed at least twenty fold higher in no more than two cell types than any other cell types. In some instances, the RNA is expressed at least five fold higher in no more than three cell types than any other cell types. In some instances, the RNA is expressed at least ten fold higher in no more than three cell types than any other cell types. In some instances, the RNA is expressed at least twenty fold higher in no more than three cell types than any other cell types.

In some aspects, the present disclosure provides for methods comprising quantifying RNA, or a cDNA thereof, in a sample of a subject. Some methods comprising amplifying the RNA, or cDNA thereof, before quantifying. Some methods comprising amplifying the RNA while quantifying. In some instances, amplifying comprises hybridizing the RNA or cDNA with a random hexamer. In some instances, amplifying comprises hybridizing the RNA or cDNA with a sequence specific primer. In some instances, amplifying comprises a thermocycling reaction. In some instances, amplifying comprises an isothermal reaction. In some instances, amplifying comprises strand displacement amplification.

Systems

In some aspects, the present disclosure provides for systems that deplete biological fluid samples of cells, cell fragments, and extracellular microparticles, in order to improve detection or quantification of nucleic acids in the biological fluids. Some systems are capable of removing additional components of the biological fluids, e.g., ribosomal RNA, mitochondrial RNA, bacterial RNA. Bacterial RNA may come from the gut. In some instances, the nucleic acids comprise RNA. In some instances, the nucleic acids consist essentially of RNA. In some instances, the RNA is messenger RNA.

In some aspects, the present disclosure provides for systems that capture extracellular microparticles in a biological fluid sample that are from non-blood tissues, including solid tissues or solid organs. In some aspects, the present disclosure provides for capturing extracellular microparticles from cells that are not circulating cells. In some aspects, the present disclosure provides for capturing extracellular microparticles from cells that are not blood cells.

In some aspects, the present disclosure provides for systems comprising a mixture of binding moieties that are capable of binding extracellular microparticles in a sample of a subject. In some instances, the binding moiety interacts with a protein on the surface of an extracellular microparticle. In some instances, the binding moiety is a receptor or a ligand for the protein on the surface of the extracellular microparticle. In some instances, the binding moiety is a binding protein that interacts with the protein on the surface of the extracellular microparticle. In some instances, the binding moiety is a small molecule. In some instances, the binding moiety is an aptamer or nucleic acid. In some instances, the binding moiety is a lipid, fatty acid, sterol or other biopolymer. In some instances, the binding moiety is an antibody. In some instances, the binding moiety is antigen-binding antibody fragment.

In some instances, the extracellular microparticle is from a blood cell. In some instances, the binding moiety interacts with or binds a protein on the extracellular microparticle that is a cell surface marker on a blood cell. Non-limiting examples of a blood cell are a T cell, a B cell, a dendritic cell, a natural killer cell, a stem cell precursor, a macrophage, a monocyte, a granulocyte, a platelet, an erythrocyte, a circulating endothelial cell, and a circulating epithelial cell. In some instances, the cell is a platelet. In some instances, the cell is a granulocyte. Non-limiting examples of cell surface markers on blood cells include GypA, CD3, CD4, CD8, CD14, CD19, CD20, CD11c, CD123, CD56, CD34, CD14, CD33, CD66b, CD41, CD42b, CD61, CD62, CD138, CD235a, CD146 or CD326.

In some instances, the binding moiety interacts with or binds a protein on the extracellular microparticle that is a cell surface marker on a non-blood cell. Non-limiting example of non-blood cell types are astrocytes, hepatocytes, and adipocytes. The non-blood cell may be from a solid tissue or a solid organ. Non-limiting examples of solid tissues include liver, adipose, kidney, pancreas, heart, muscle, bone marrow, skin, prostate, testes, breast, ovary, uterus, colon, lung, and neurological tissue. Non-limiting examples of cell surface markers on liver cells include ASGR1 and GFAP. Non-limiting examples of cell surface markers on adipose cells are SLC7A10 and FABP4. Non-limiting examples of cell surface markers on astrocytes include GLAST. Non-limiting examples of cell surface markers on kidney cells (e.g., renal tubular cells) include gamma-glutamyl-transpeptidase.

Some systems comprise a plurality of binding moieties that interact with a plurality of proteins on the surface a plurality of extracellular microparticles. In some instances, systems comprise at least two binding moieties. In some instances, systems comprise at least three binding moieties. In some instances, systems comprise at least four binding moieties. In some instances, systems comprise about two binding moieties to about five binding moieties. Some systems comprise a first binding moiety and a second binding moiety. In some instances, the first binding moiety interacts with a first protein on a first cell and a second antibody interacts with a second protein on a second cell. In some instances the first binding moiety and the second binding moiety are different. In some instances, the first protein and the second protein are the same. For instance, in some cases, the first binding moiety and the second binding moiety target the same protein, but both are used, because there is uncertainty about which binding moiety will work best in the subject's sample. In some instances, the first protein and the second protein are different. In some instances, the first protein and the second protein are different by at least about 10 amino acids. In some instances, the first protein and the second protein are different by at least about 100 amino acids. In some instances, the first protein and the second protein are different by at least about 200 amino acids. In some instances, the first protein and the second protein are different by at least about 400 amino acids. In some instances, the first protein and the second protein are expressed from different genes. In some instances, the first protein is not expressed on the second cell and the second protein is not expressed on the first cell. In some instances, the first cell and the second cell are two different types of leukocytes. In some instances, the plurality of binding moieties is capable of binding or interacting with extracellular microparticles from at least two different cell types.

Some systems comprise a plurality of binding moieties that interact with a plurality of proteins on the surface a plurality of extracellular microparticles. In some instances, the plurality of binding moieties is capable of binding or interacting with extracellular microparticles from at least two different cell types. In some instances, the plurality of binding moieties is capable of binding or interacting with extracellular microparticles from at least three different cell types. In some instances, the plurality of binding moieties is capable of binding or interacting with extracellular microparticles from at least four different cell types. In some instances, the plurality of binding moieties is capable of binding or interacting with extracellular microparticles from at least five different cell types. In some instances, the plurality of binding moieties is capable of binding or interacting with extracellular microparticles from at least two different types of circulating cells or blood cells. In some instances, the plurality of binding moieties is capable of binding or interacting with extracellular microparticles from at least three different types of circulating cells or blood cells. In some instances, the plurality of binding moieties is capable of binding or interacting with extracellular microparticles from at least four different types of circulating cells or blood cells. In some instances, the plurality of binding moieties is capable of binding or interacting with extracellular microparticles from at least five different types of circulating cells or blood cells. Non-limiting examples of types of circulating cells or blood cells include lymphocytes, T cells, B cells, dendritic cells, natural killer cells, stem cell precursors, macrophages, monocytes, granulocytes, platelets, erythrocytes, circulating endothelial cells, and circulating epithelial cells.

Some systems disclosed herein comprise a solid support, wherein at least one binding moiety is attached to the solid support. In some instances, the binding moiety is connected to the solid support. In some instances, the binding moiety is conjugated to the solid support. In some instances, the binding moiety interacts with the solid support. Non-limiting examples of a solid support are a bead, a column, a plate, or an array. In some instances, the binding moiety has an affinity for a solution that is immiscible with the sample, such that when the solution is added to the sample after contacting the sample with the binding moiety, the binding moiety separates into the solution, thereby removing the extracellular particle from the sample. In some instances, the system comprises the solution.

In some instances, the systems disclosed herein comprise a container for a sample of a subject. The container may contain EDTA. The container may not contain EDTA. The sample may contain cells. Some systems comprise a cell-separation component for separating the cells from the sample of the subject. In some instances, the cell-separation component is a machine that rotates the container to apply centrifugal force to the container, thereby removing at least a portion of cells from the blood sample. Alternatively, or additionally, systems comprise a filter for removing the cells. In some instances, the filter removes cell fragments, extracellular microparticles, or other components of the sample. Generally the filter is suitable for separating these components from circulating cell-free messenger RNA in the sample. In some instances, the filter has a pore diameter of about 200 microns to about 800 microns. In some instances, the filter has a pore diameter of about 800 microns to about 2000 microns. In some instances, the filter has a pore diameter of about 400 microns to about 1200 microns. In some instances, the filter has a pore diameter of about 600 microns to about 1000 microns. In some instances, the filter has a pore diameter of about 800 microns.

Some systems disclosed herein comprise at least one reagent for quantifying a nucleic acid present in a sample from a subject. In some instances, the nucleic acid is RNA. In some instances, the RNA is messenger RNA. In some instances, the nucleic acid is complementary DNA (cDNA). In some instances, the reagent is an oligonucleotide that is complementary to a nucleic acid of interest. In some instances, the reagent is a reverse transcriptase, and the system is used to reverse transcribe the RNA to a cDNA. In some instances, the reagent is an oligonucleotide that is complementary to the cDNA. In some instances, the system comprises two oligonucleotides capable of amplifying the RNA or cDNA. In some instances, the reagent is an enzyme that amplifies the nucleic acid. In some instances the systems comprise a machine or reagent necessary for producing and/or reading Q-PCR or sequencing readout. Such machines and reagents are well known in the art.

In some instances, the systems and methods described herein comprise use of deconvolution by relative entropy maximization: methods to quantify relative amount of a specific cell type/tissue/organ of interest from a complex mixture, such as cell-free RNA, based gene expression measurements of the mixture.

Given a mixture of RNA from different tissues, the method solves for p, a vector of proportions of tissues that makes up the mixture, using gene expression values of the mixture as well as gene expression values in each of the tissues. The objective of this method is to find value of p that minimizes the sum of 1) relative entropy between observed expression profile in mixture and linear combination of tissue expression profiles weighted by p and 2) L2-norm penalty function under the constraint that values of p must sum to one.

As the goal is to estimate a probability distribution over tissue contributions, optimization must be performed under the constraint that probabilities over all tissues must sum to one. In current implementation, this constraint that probability over n tissues sums to one is satisfied by choosing a reference tissue a priori, then estimate n−1 free parameters, representing log ratio of contribution of a particular tissue relative to the reference tissue. Log ratios can then be converted to probabilities after parameter estimation is completed. Reference tissue are chosen to be tissue that are likely to be highly represented in the mixture so that estimated log ratio are numerically stable. Other approaches, such as the use of constrained optimization methods are also possible, but they may be more prone to numerical difficulties.

A feature selection step is performed before deconvolution. A feature matrix is constructed from tissue gene expression profiles. Features, which can be genes or weighted linear combination of genes, are chosen to be tissue specific.

Highly correlated genes can be combined together to create new features which reduces noise and reduce multicollinearity.

P-Value of the Fit can be Calculated Using a Log Ratio Test

More precisely, given a n by f feature matrix F, where n is total number of tissues and f is total number of features, and f-long vector of observed expression profile O, we find values of P that minimizes $$\sum_{i=1}^{f} O_i \log\left(\frac{Q_i}{O_i}\right) + \lambda \sum_{j=1}^{n} P_j^2$$

where Q is F-long vector of predicted expression profile from current values of P, $$Q=FP$$

Numbered Embodiments

The disclosure is further understood through review of the numbered embodiments recited herein. 1. A method comprising obtaining a blood sample from a subject; centrifuging or filtering the blood sample to obtain a plasma sample; filtering the plasma sample to remove platelets from the plasma sample, thereby producing a cell-depleted sample; contacting the cell-depleted sample with a cell-surface protein binding moiety, wherein the cell-surface protein binding moiety is capable of binding a cell-surface protein on a blood-cell exosome in the cell-depleted sample; removing the cell-surface protein binding moiety from the cell-depleted sample, thereby removing the blood-cell exosome from the cell-depleted sample; and quantifying circulating cell-free RNA in the cell-depleted sample, wherein the cell-free RNA is expressed by a tissue of interest. 2. A method comprising: obtaining a blood sample from a subject; removing cells from the blood sample to obtain a cell-depleted sample; removing an extracellular microparticle from the blood sample to obtain a microparticle-depleted sample; quantifying an amount of RNA corresponding to a gene in the microparticle-depleted sample. 3. The method of embodiment 1 or 2, wherein the removing the extracellular microparticle comprises contacting the cell-depleted sample with a binding moiety that interacts with a protein on the surface the extracellular microparticle. 4. The method of embodiment 1 or 2, wherein the binding moiety is an antibody or antigen-binding antibody fragment. 5. The method of embodiment 4, wherein the antibody or antigen-binding antibody fragment is attached to a support. 6. The method of embodiment 4, wherein the antibody interacts with a cell surface marker known to be expressed by a blood cell. 7. The method of embodiment 6, wherein the blood cell is a leukocyte. 8. The method of embodiment 7, the antibody comprises an anti-CD45 antibody. 9. The method of embodiment 6, wherein the blood cell is a granulocyte. 10. The method of embodiment 9, wherein the antibody comprises an anti-CD66b antibody. 11. The method of embodiment 4, comprising contacting the cell-depleted sample with a first antibody that interacts with a first protein on a first cell and a second antibody that interacts with a second protein on a second cell. 12. The method of embodiment 11, wherein the first protein and the second protein are different by at least 10 amino acids. 13. The method of embodiment 11, wherein the first protein and the second protein are expressed from different genes. 14. The method of embodiment 11, wherein the first protein is not expressed on the second cell and the second protein is not expressed on the first cell. 15. The method of embodiment 11, wherein the first cell and the second cell are two different types of leukocytes. 16. The method of embodiment 1 or 2, wherein quantifying comprises quantifying a relative contribution of the RNA to the microparticle-depleted sample. 17. The method of embodiment 1 or 2, wherein quantifying comprises sequencing the RNA. 18. The method of embodiment 1 or 2, wherein the RNA is expressed more highly in a tissue of interest than any other tissue of the subject. 19. The method of embodiment 18, wherein the tissue of interest is neurological tissue. 20. The method of embodiment 18, wherein the tissue of interest is liver, adipose, kidney, or neurological tissue. 21. The method of embodiment 1 or 2, wherein removing cells comprises centrifuging or filtering blood. 22. The method of embodiment 2, wherein removing cells comprises filtering the cell-depleted sample to remove platelets. 23. The method of embodiment 1 or 2, comprising amplifying the RNA or a cDNA thereof to produce an amplified nucleic acid. 24. The method of embodiment 23, wherein the amplifying comprises hybridizing the RNA or cDNA with a random hexamer. 25. The method of embodiment 1 or 2, wherein the RNA comprises messenger RNA. 26. The method of embodiment 1, 2 or 23, wherein quantifying comprises sequencing the RNA, cDNA or amplified nucleic acid. 27. The method of embodiment 1 or 2, wherein the RNA is more highly expressed in a tissue of interest than it is expressed in blood. 28. The method of embodiment 1 or 2, wherein the extracellular microparticle is an exosome. 29. The method of embodiment 28, wherein the exosome is from a blood cell. 30. The method of embodiment 29, wherein the blood cell is a platelet. 31. The method of embodiment 30, wherein removing the extracellular microparticle comprises contacting the cell-depleted sample with an anti-GypA antibody or GypA antigen-binding fragment thereof 32. The method of embodiment 29, wherein the blood cell is a red blood cell. 33. The method of embodiment 32, wherein removing the extracellular microparticle comprises contacting the cell-depleted sample with an anti-CD235a antibody or CD235a antigen-binding fragment thereof 34. The method of embodiment 29, wherein the blood cell is a granulocyte. 35. The method of embodiment 34, wherein removing the extracellular microparticle comprises contacting the cell-depleted sample with an anti-CD66b antibody or CD66b antigen-binding fragment thereof 36. The method of embodiment 29, wherein the blood cell is a lymphocyte. 37. The method of embodiment 36, wherein removing the extracellular microparticle comprises contacting the cell-depleted sample with an antibody or antigen-binding fragment thereof that binds CD45, CD19 or CD3. 38. The method of embodiment 1 or 2, wherein the RNA is not attached to a cell, an exosome, or a fragment thereof 39. The method of embodiment 1 or 2, wherein the cell-depleted sample is depleted of at least 90% of cells in the blood sample. 40. The method of embodiment 1 or 2, wherein the cell-depleted sample comprises plasma or serum. 41. The method of embodiment 1 or 2, wherein the cell-depleted sample consists essentially of plasma or serum. 42. The method of embodiment 41, comprising purifying the RNA from the plasma or serum. 43. The method of embodiment 42, wherein the plasma or serum is incubated 1 h at 60 degrees Celsius. 44. The method of embodiment 43, comprising incubating in a presence of a chaotropic salt, detergent, proteinase K, 2-mercaptoethanol, or a combination thereof 45. The method of embodiment 43 or 44, comprising incubating the sample with Tris. 46. The method of any one of embodiments 43-45, comprising disrupting lipidic and proteinaceous structures. 47. The method of embodiment 42, comprising contacting the plasma or serum with a silica column. 48. The method of embodiment 47, comprising incubating the samples with chaotropic salts and 100% isopropanol to enhance the binding of RNA to a silica column. 49. The method of embodiment 48, comprising passing the sample through the silica column using a vacuum manifold. 50. The method of embodiment 49, comprising washing the sample with low concentration chaotropic salts and ethanol. 51. The method of embodiment 50, comprising washing the sample with 100% ethanol wash to remove impurities and inhibitors in the sample. 52. The method of embodiment 48, comprising eluting RNA from the silica column with low-ionic buffers or water. 53. The method of embodiment 52, comprising incubating the eluted RNA for 20 min with a highly pure, inhibitor resistant, recombinant DNase with a very high catalytic efficiency to eliminate any DNA. 54. The method of embodiment 53, comprising passing the RNA through an inhibitor removal column that eliminates contaminants and inhibitors. 55. The method of embodiment 53, comprising binding the RNA to a silica membrane using chaotropic salts and 66% ethanol, washing the RNA and eluting. 56. The method of embodiment 55, comprising eluting with water. 57. A method of enriching for circulating non-blood RNA in a blood sample, comprising depleting the blood sample of blood cells; and depleting the blood sample of exosomes. 58. A method of enriching for circulating non-blood RNA in a blood sample, comprising depleting the blood sample of blood cells to produce a cell-depleted blood sample; and contacting the cell-depleted blood sample with a blood cell surface binding moiety. 59. The method of embodiment 57 or 58, wherein depleting comprises filtering the blood sample to remove the blood cells. 60. The method of embodiment 59, wherein the blood cells comprise platelets. 61. The method of embodiment 57 or 58, wherein depleting comprises centrifuging the blood sample. 62. The method of embodiment 57 or 58, wherein the method depletes the blood sample of at least 90% of the cells that were originally present in the blood sample. 63. The method of embodiment 57 or 58, wherein the method depletes the blood sample of at least 99% of the cells that were originally present in the blood sample. 64. The method of embodiment 57 or 58, wherein the method depletes the blood sample of at least 90% of extracellular microparticles that were originally present in the blood sample. 65. The method of embodiment 57 or 58, wherein the method depletes the blood sample of at least 99% of extracellular microparticles that were originally present in the blood sample. 66. The method of embodiment 57 or 58, wherein the non-blood RNA is from a solid organ. 67. The method of embodiment 66, wherein the solid organ is liver, adipose, kidney or brain. 68. The method of embodiment 67, wherein the solid organ in brain or spinal cord. 69. The method of embodiment 57 or 58, wherein the non-blood RNA is from a non-blood cell type. 70. The method of embodiment 69, wherein the non-blood cell type is an oligodendrocyte. 71. The method of embodiment 57 or 58, comprising quantifying the non-blood RNA. 72. The method of embodiment 71, wherein quantifying comprises at least one methods selected from quantitative-PCR and sequencing. 73. A system comprising: a container for a blood sample of a subject; a machine that rotates container to apply centrifugal force to the container, thereby removing at least a portion of cells from the blood sample; a filter for removing platelets from the blood sample; and an antibody that interacts with a protein on an extracellular microparticle. 74. The system of embodiment 73, comprising a plurality of antibodies. 75. The system of embodiment 73, wherein the plurality of antibodies comprises at least one of CD45, CD66b, GypA, CD235a, CD19, and CD3. 76. The system of embodiment 73, wherein the antibody is attached to a support that can contact the blood sample and be removed from the blood sample, thereby removing the extracellular microparticle from the blood sample. 77. The system of embodiment 73, comprising at least one reagent for quantifying an RNA present in the blood sample. 78. A method comprising: obtaining a blood sample from a subject; centrifuging or filtering the blood sample to obtain a plasma sample; contacting the plasma sample with a cell-surface protein binding moiety, wherein the cell-surface protein binding moiety is capable of binding a cell-surface protein on an extracellular microparticle in the plasma sample, wherein the extracellular microparticle is from a tissue of the subject; removing the cell-surface protein binding moiety from the cell-depleted sample, thereby removing the extracellular microparticle from the cell-depleted sample; and quantifying an RNA in the extracellular microparticle, wherein the RNA is expressed by the tissue of interest. 79. The method of embodiment 78, wherein the tissue is a solid organ. 80. The method of embodiment 78, wherein the cell-surface protein binding moiety is an antibody or antigen-binding fragment thereof 81. The method of embodiment 78, wherein the tissue is liver. 82. The method of embodiment 80, wherein the cell-surface protein is asialoglycoprotein receptor 1 (ASGR1), or Glial fibrillary acidic protein (GFAP). 83. The method of embodiment 78, wherein the tissue is adipose. 84. The method of embodiment 83, wherein the cell-surface protein is SLC7A10 or fatty acid binding protein 4 (FABP4). 85. The method of embodiment 78, wherein the tissue is neurological tissue. 86. The method of embodiment 85, wherein the cell-surface protein is glutamate aspartate transporter (GLAST). 87. The method of embodiment 78, wherein the tissue is kidney. 88. The method of embodiment 87, wherein the cell-surface protein is gamma-glutamyl-transpeptidase.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Isolation of Cell Free RNA

V2 extraction method: Blood samples were collected in EDTA tubes, centrifuged at 1900 g for 10 min. Plasma was separated into a new tube (platelet rich plasma in FIG. 3). To remove platelets the plasma was subsequently centrifuged at 16000 g and pass through a 0.8 μm filter. In some cases, the plasma was frozen and thawed at 37° C. To purify nucleic acids from plasma, samples were incubated 1 h at 60 C in presence of high concentration of chaotropic salts, detergents, proteinase K and 2-mercaptoethanol in a Tris background to disrupt lipidic and proteinaceous structures. After the lysis, additonal chaotropic salts and isopropanol 100% were added to the sample to enhance the binding of nucleic acids to a silica column. Sample was passed through the silica membrane using a vacuum manifold. Sample was thoroughly washed with low concentration chaotropic salts and ethanol, in addition to a 100% ethanol wash to remove impurities and inhibitors (polysaccharides, biosalts, proteins). Nucleic acids were eluted with low-ionic buffers or water. Subsequently, samples were incubated for 20 min with a highly pure, inhibitor resistant, recombinant DNase with a very high catalytic efficiency to eliminate any DNA. To prevent inhibition of the reverse transcriptase reaction in downstream applications cfRNA was pass through an inhibitor removal column that eliminates contaminants and inhibitors (polyphenols, humic acids). To remove remaining enzymes and impurities and concentrate the cfRNA the sample was bound to a silica membrane using chaotropic salts and 66% ethanol, washed and eluted in 15 ul of water. The amount, size and integrity of cfRNA were estimated by running 1 ul of the sample in an Agilent RNA 6000 Pico chip using a 2100 Bioanalyzer (Agilent Technologies Inc., La Jolla, CA).

Figure 3:
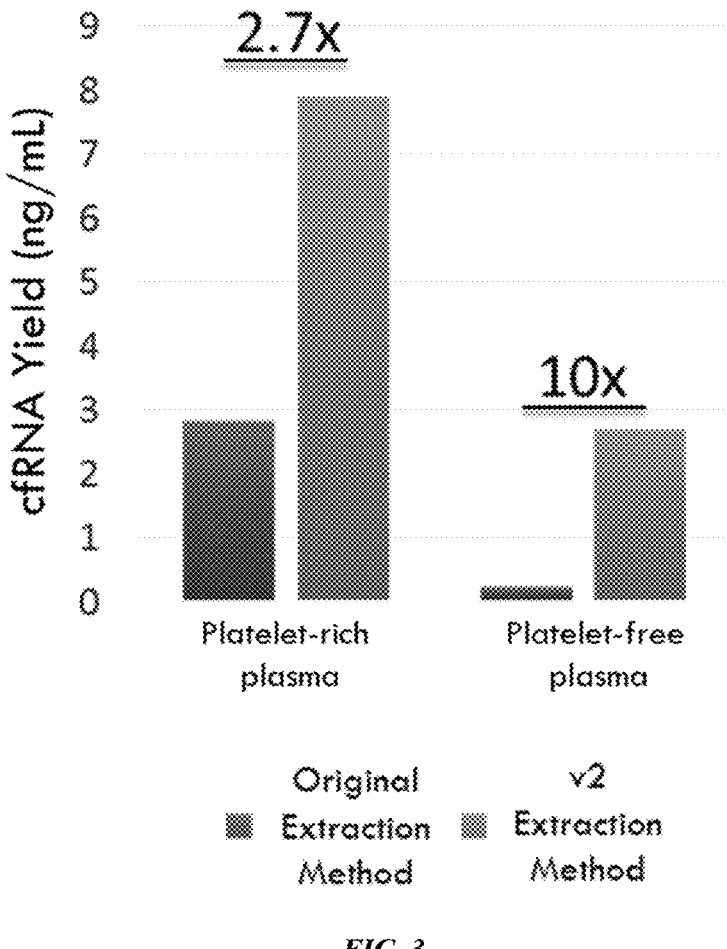
FIG. 3 shows increased cell free RNA yield using methods disclosed herein.
Figure 4A:
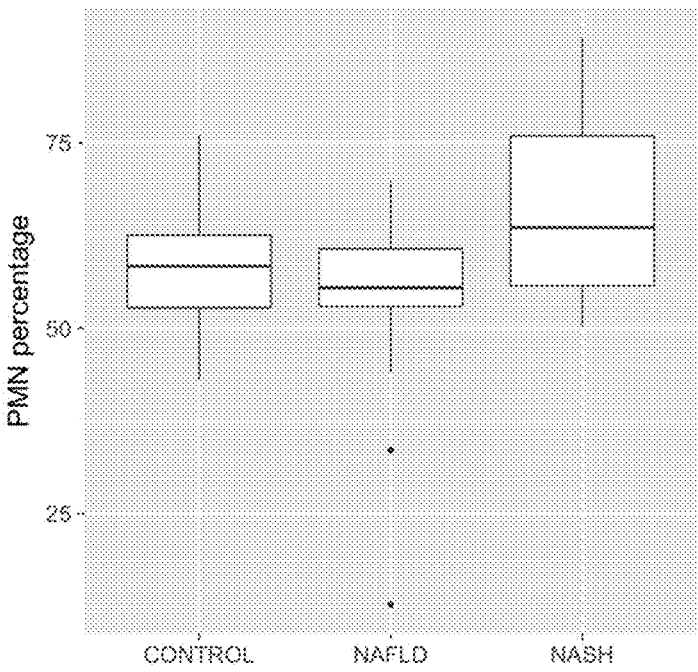
FIG. 4A shows polymorphonuclear (PMN) leukocyte transcripts track with disease severity (NAFLD=non alcoholic fatty liver disease, NASH=non-steatotic hepatitis).
Figure 4B:
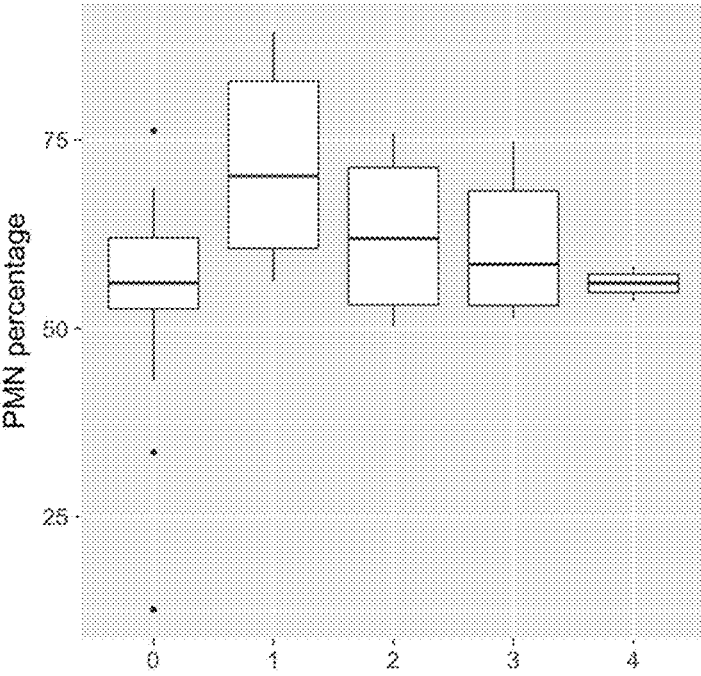
FIG. 4B shows extent of transcriptome which is accounted for by PMNs.

This method can be compared to previously known methods, also referred to herein as old extraction method (see FIG. 3). An example of previously known methods are as follows. 1 ml of plasma was thawed at room temperature and incubated for 30 min at 55 C in the presence of 2M GTC, 120 mM Tris-HCl, 20 mM CaCl2, 2% Tween20, 1% Triton X-100, 2-mercaptoethanol and 200 ul of proteinase K (20 mg/ml). After the lysis, chaotropic salts and ethanol was added and the sample spun down through a silica-based matrix. After washing with 2.5M GTC, 50 mM Citrate, and 37.7% ethanol nucleic acids were eluted in water. Subsequently, sample was treated with DNaseI endonuclease for 30 min at 37 C. Last, sample was bound to a silica matrix using 33% ethanol and chaotropic salts, washed and eluted in 15 ul of water. The amount of mRNA was estimated by qPCR using the SuperScript III reverse transcriptase, Platinum DNA polymerase and SYBR Green. The human 18S transcript was used as surrogate for estimating RNA concentration (18S_F: SEQ ID NO: 1; 18S-reverse: SEQ ID NO: 2; Integrated DNA Technologies, WCO., San Diego, CA). Human brain tissue total RNA was used to generate a calibration curve (FirstChoice Human Brain Reference Total RNA, Thermo Fisher Scientific, Inc.). Real-time quantitative PCR was performed on a CFX96 Touch Real-Time PCR Detection System (Bio-Rad Laboratories, Inc., Hercules, CA).

Example 2. Immunodepletion and Enrichment of Cell Free Nucleic Acids

A plasma sample was obtained from a subject. The plasma contained exosomes from multiple types of blood cells. Plasma was incubated with CD45 antibody. Magnetic particles targeting CD45 antibody were added to the plasma sample. A magnet was used to remove the magnetic particles and bound structures, leaving unbound exosomes behind. The resulting sample contained fewer transcripts from mononuclear blood cells after removal of exosomes, demonstrating 10 fold depletion of the transcripts from this cell type as shown in Table 1, as measured by RNA sequencing.

The samples were analyzed by sequencing and the table below shows % of reads represented by a particular cell type. For example mononuclear cells (Lymphocytes and monocytes) account for _8.831% of cells prior to depletion and 0.893% after depletion.

TABLE 1

Fractions of tissue specific transcripts
before and after exosome removal

| Tissue represented as fraction of all queried transcripts | Before CD45 antibody | After CD45 antibody |
|---|---|---|
| Red blood cells | 5.09 | 7.972 |
| Platelets | 44.388 | 47.879 |
| Polymorphonuclear cells (PMNs) | 39.749 | 39.283 |
| Mononuclear cells | 8.831 | 0.893 (10 fold decrease) |
| Oligodendrocytes | 0.103 | 0.105 |
| Liver | 0.08 | 0.244 (3 fold increase) |
| Neurons | 0.014 | 0.015 |
| Artery | 0.001 | 0.001 |
| Adipose | 0.019 | 0.023 |
| Bone marrow | 1.244 | 2.699 |
| Kidney | 0.039 | 0.035 |
| Lung | 0.348 | 0.532 |
| Skeletal muscle | 0.001 | 0.002 |
| Heart | 0.005 | 0.01 |
| Hippocampus | 0.087 | 0.308 |

Example 3. Evaluating Q-PCR Efficiency for Quantifying Cell-Free RNA

Figure 5:
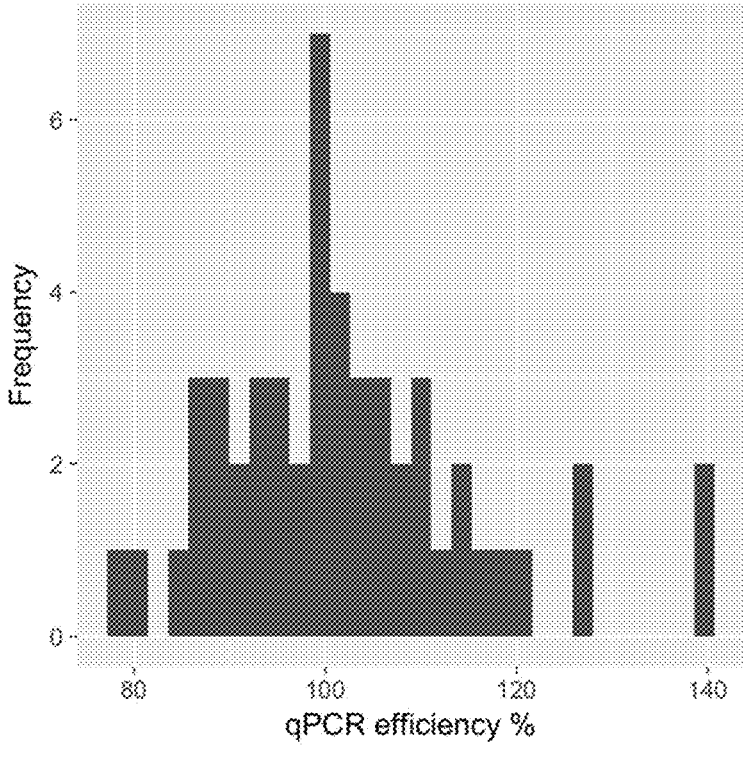
FIG. 5 shows qPCR primer efficiency calculated from titration of liver tissue RNA.
Figure 6:
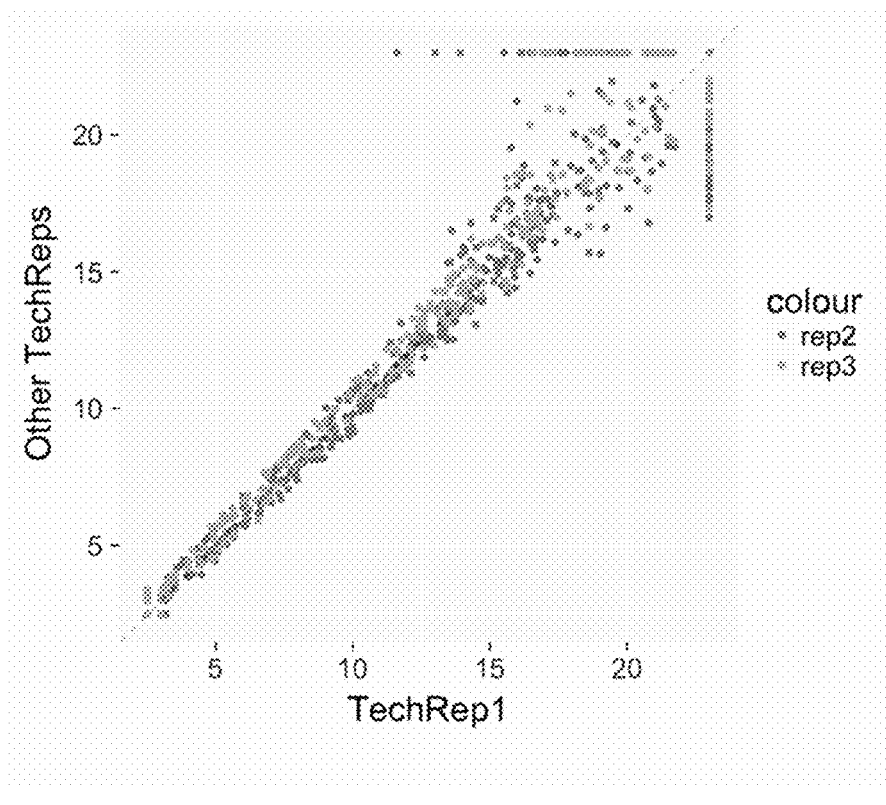
FIG. 6 shows excellent reproducibility of qPCR quantification of non-blood cell transcripts with samples processed according to methods described herein.
Figure 7:
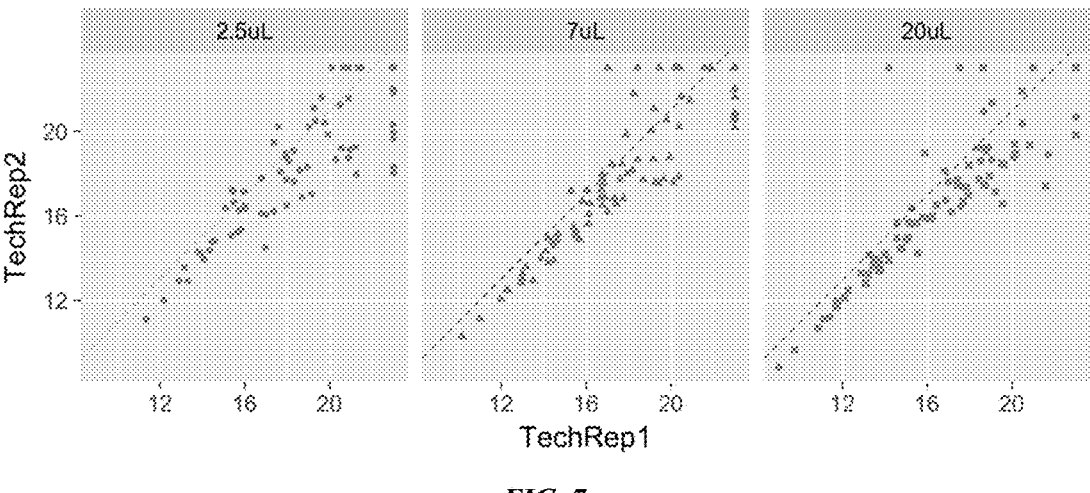
FIG. 7 shows reproducibility improves as a function of input.
Figure 8:
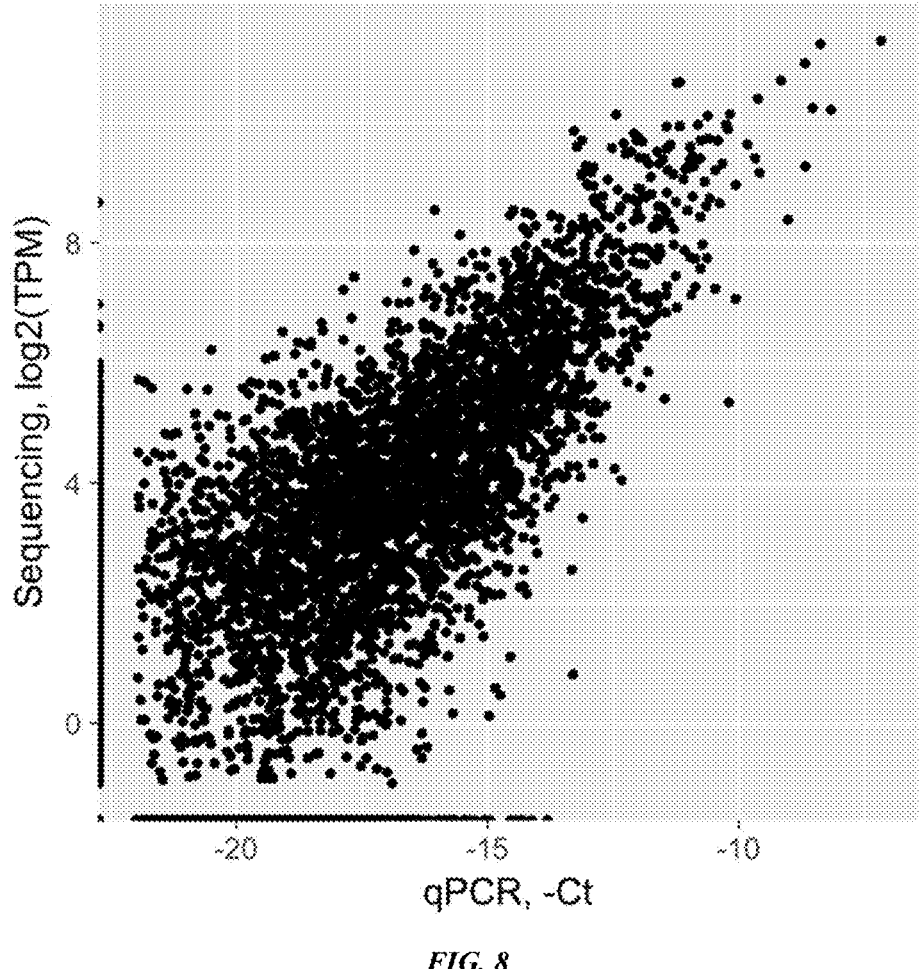
FIG. 8 shows a correlation between sequencing and qPCR panel using a 65-patient NAFLD cohort. Each dot represents one of the genes in the 96-gene qPCR panel plotted by sequencing (log 2 TPM) and qPCR (negative Ct) detection for each patient. For each sample, half of extracted RNA was used for qPCR, the other half was used in sequencing.
Figure 9:
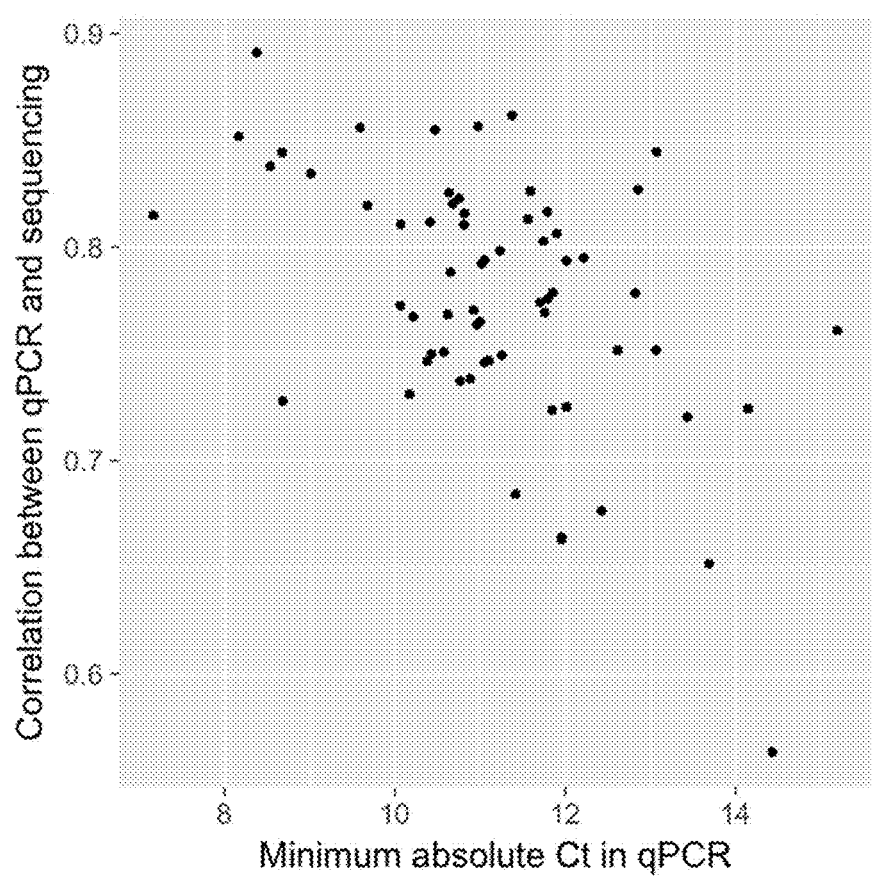
FIG. 9 shows improved correlation between qPCR and sequencing in samples with more total RNA.
Figure 10A:
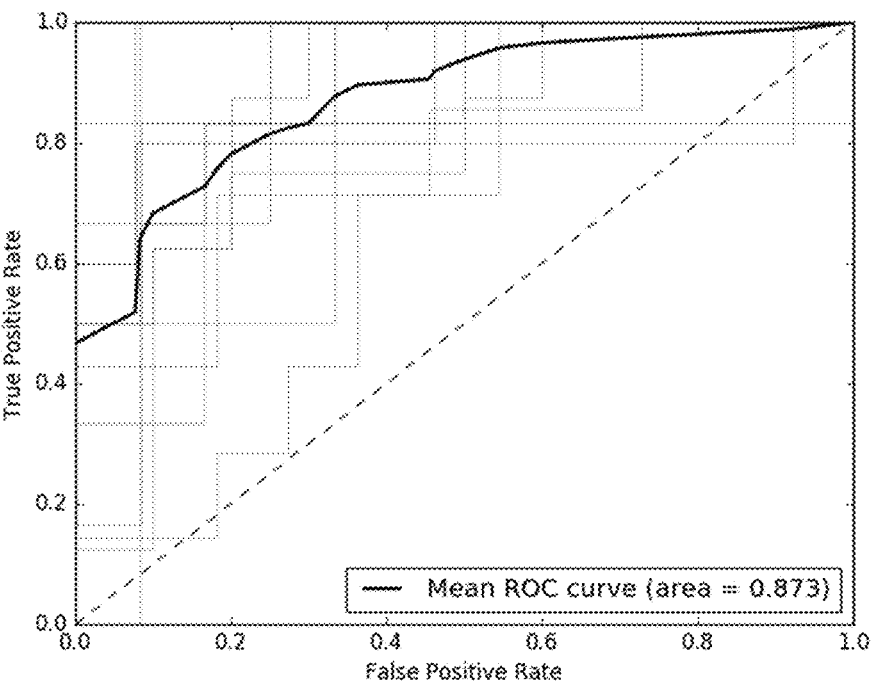
FIG. 10A shows initial classifier, NASH versus control using qPCR data from a 96 gene panel.
Figure 10B:
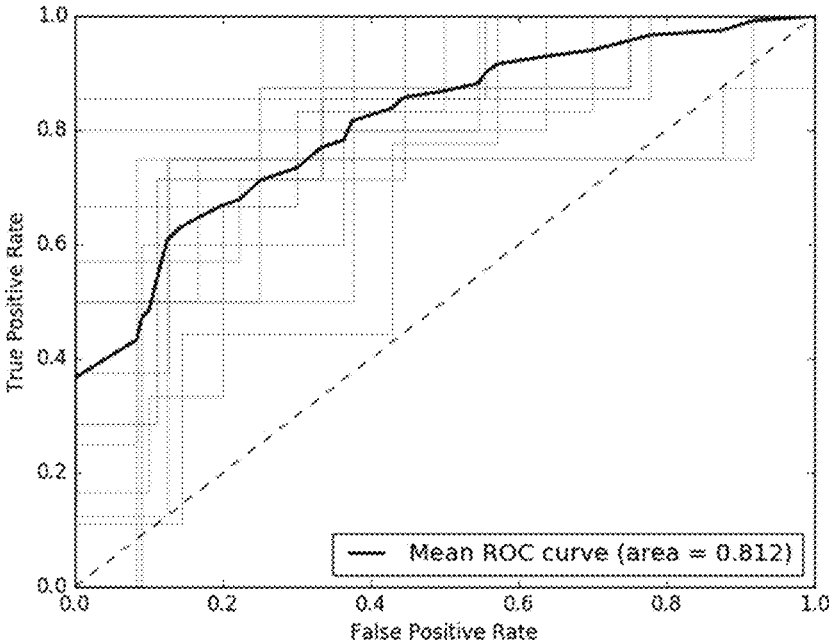
FIG. 10B shows initial classifier, NAFLD versus NASH using qPCR data from a 96 gene panel.
Figures 11C, 11D:
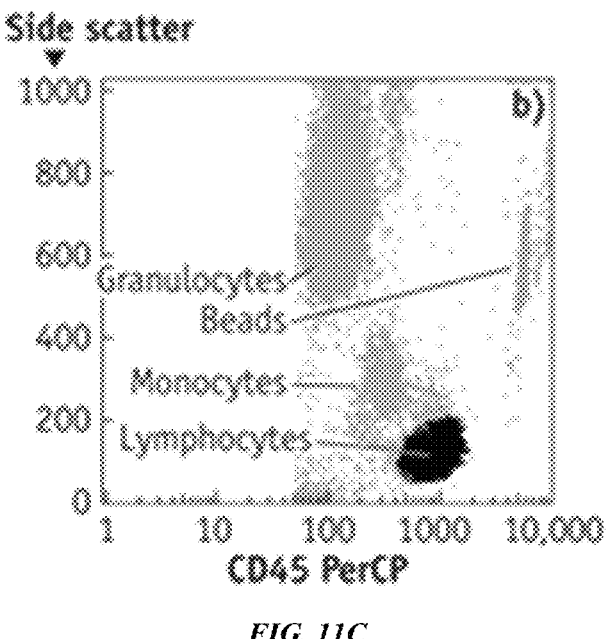
Figure 12A:
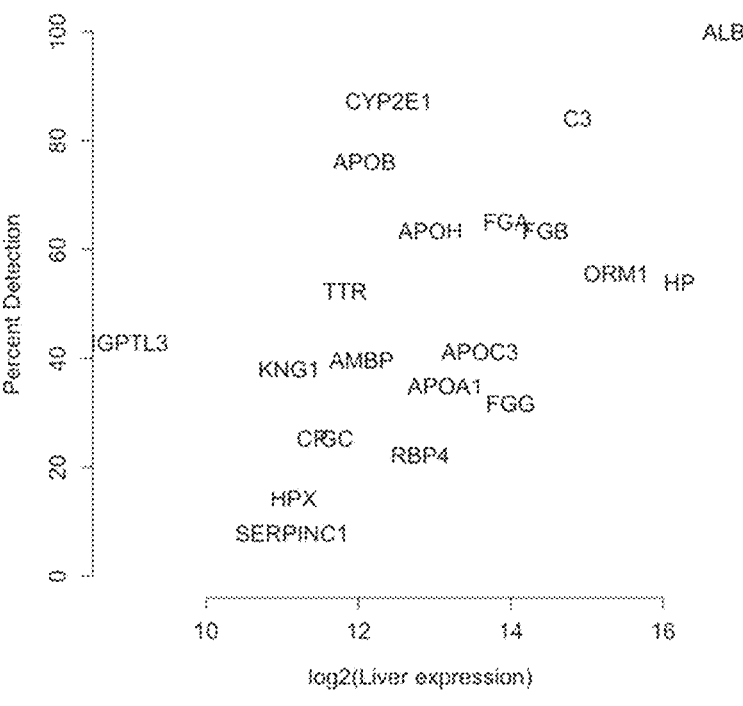
FIG. 12A-B shows sequencing assay sensitivity improvements.
Figure 12B:
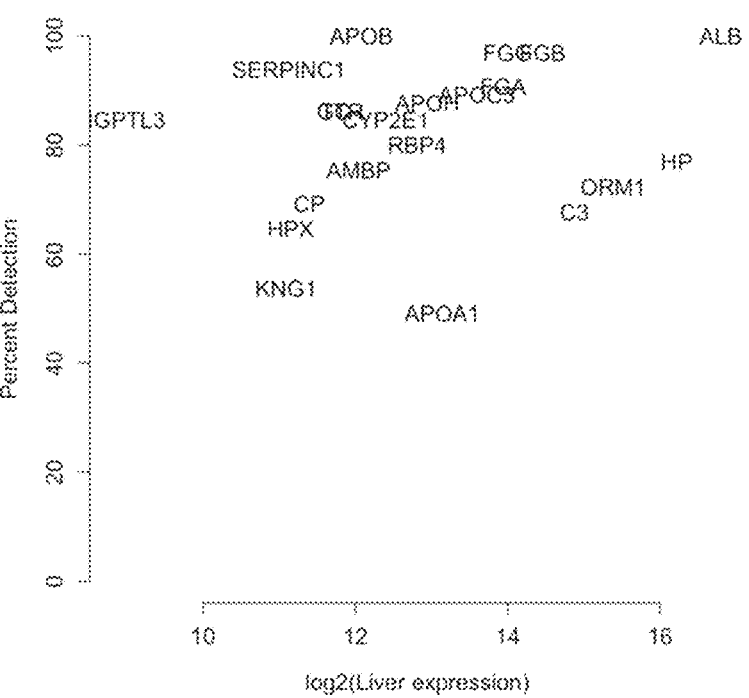
Figure 13A:
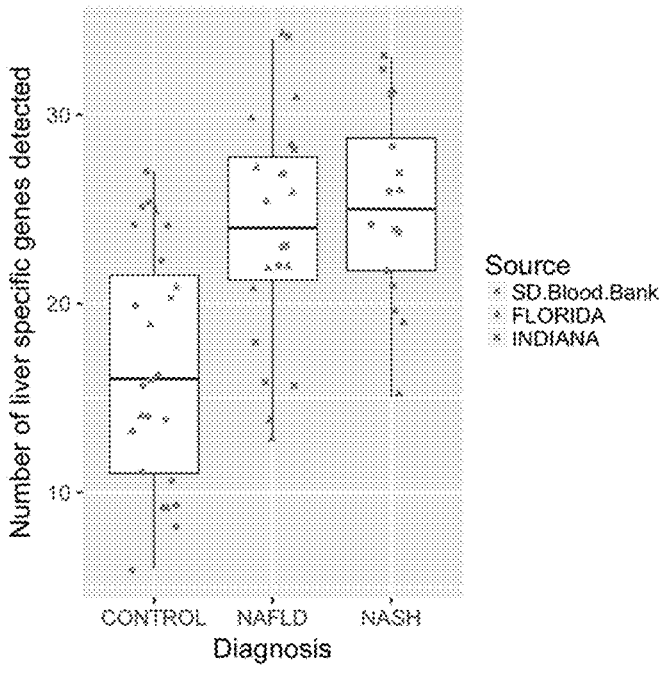
FIG. 13A shows the number of liver specific genes sequenced tracks with diagnosis and FIG. 13B shows the liver specific genes detected tracks with fibrosis score.
Figure 13B:
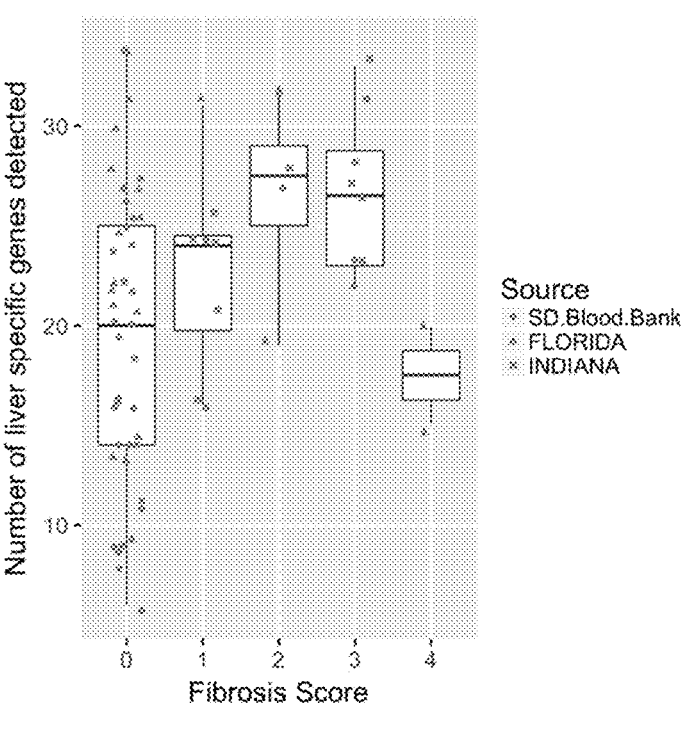
Figures 14A, 14B:
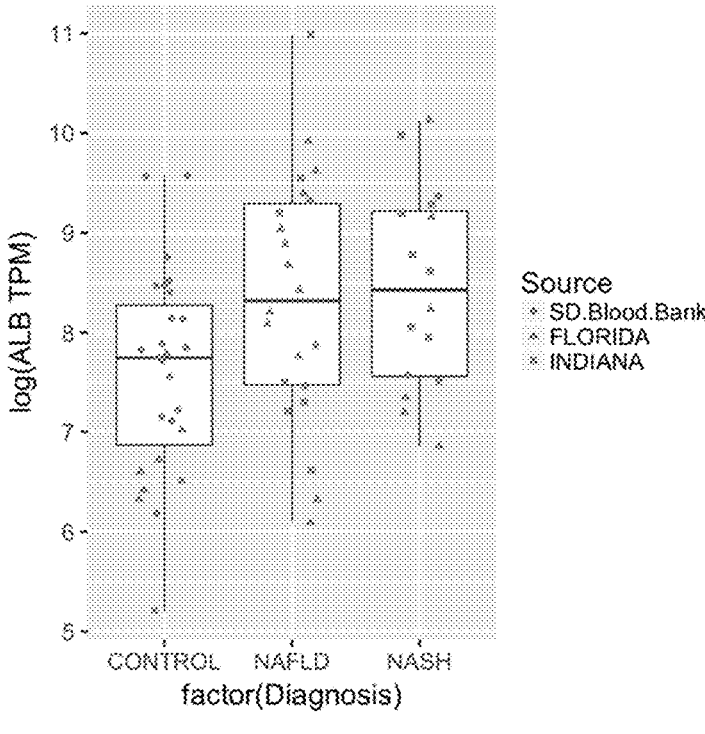
FIG. 14A shows albumin transcripts sequenced tracks with diagnosis and FIG. 14B shows the albumin transcripts detected tracks with fibrosis score.
Figure 15:
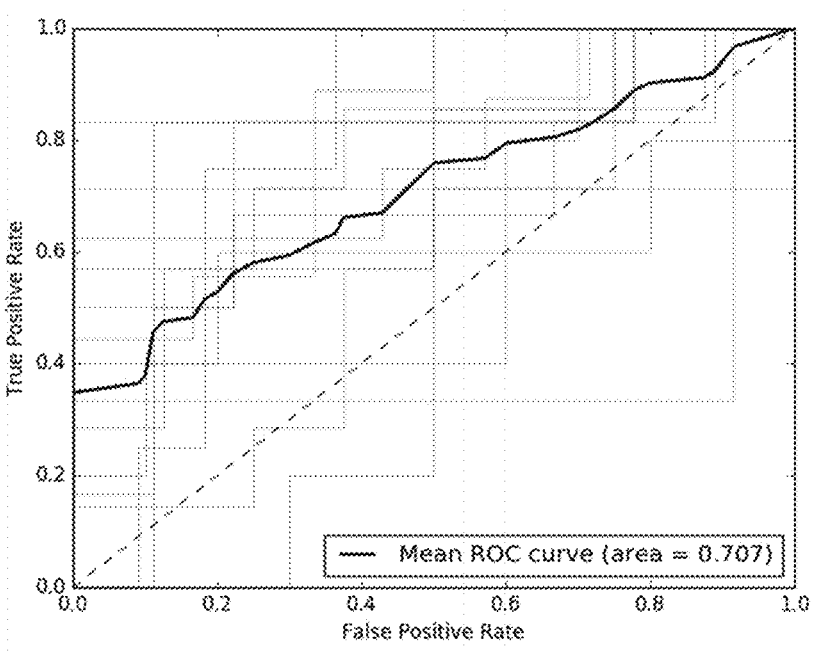
FIG. 15 shows an initial classifier: NASH vs Control using sequencing data from all genes.

Each amplicon produced from qPCR of liver mRNA was compared against titrations of liver tissue mRNA to determine the efficiency of the qPCR reaction. Efficiency is calculated as a percentage of yield compared to the doubling per cycle which would be expected for an ideal PCR reaction which would be expected to be 100%. Results are shown in FIG. 5. The x-axis is fibrosis stage. RNAs queried correspond to the following genes:

Example 4. Reproducibility Between Two PCR Replicates Starting from the Same Amount of RNA RNA was obtained from a pool of control donor plasma. The RNA from one mL of plasma is contained in 15 microliters extract. See FIG. 7 for results. Shown on the X and Y axes are the Ct counts for PCR.

Example 5: Using a Cocktail of Antibodies to Remove Multiple Blood Cell Exosomes A plasma sample is obtained from a subject. The plasma contains exosomes from multiple types of blood cells. Magnetic beads with antibodies that bind cell surface markers corresponding to the multiple types of blood cells are added to the plasma sample and incubated. Alternatively or additionally, a single antibody is used that binds to a cell surface marker that is expressed on many blood cell types. The sample is subjected to a magnet and undesired exosomes are removed from plasma sample, leaving exosomes of interest. The resulting sample contains much fewer transcripts from blood cells after removal of exosomes, increasing sensitivity of detection for tissue specific transcripts.

Nucleic acids of interest in the remaining sample are analyzed according to the following steps.

Collect: EDTA-2 spins followed by filter→decrease in platelets preferred is one low speed spin followed by high speed spin (16 k). Freeze supernatant.

Extraction: Thaw sample followed by filtration Qiagen CNA kit→10×increase yield from platelet poor plasma, smaller cfRNA species (100 base) in addition to longer transcripts Clean up: Polyphenol inhibitor removal column, off-column recombinant DNAse, clean-up column RT: SS IV 2 step with high concentration random hex-amers RQ-PCR: nested design, with different primers at preamp step containing all primers, followed by Exonuclease 1 treatment to remove single-stranded primers, followed by final amplification in separate microchambers using a single pair of nested primers for final PCR detection reaction. Nucleic acids from remaining blood cells and other organs, other than those of interest, are included for normalization.

Swift 1S is used to prepare sequencing libraries of the nucleic acids in the sample, followed by target enrichment.

Data processing: partial assembly before alignment, blood cell assignment based on entropy.

Figure 16:
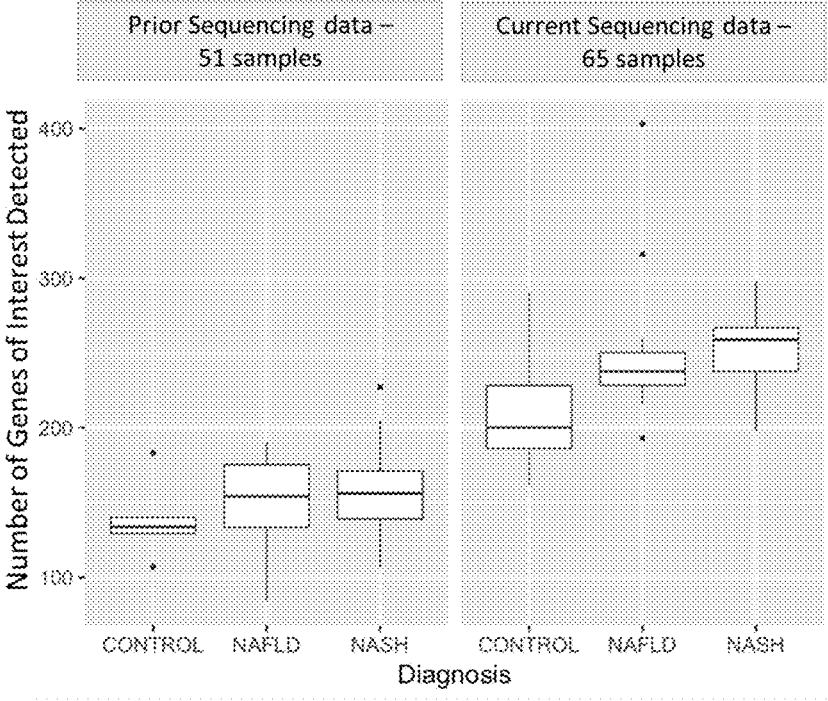
FIG. 16 shows methods, systems and kits disclosed herein allow for detection of ~250 genes of interest.
Figure 17A:
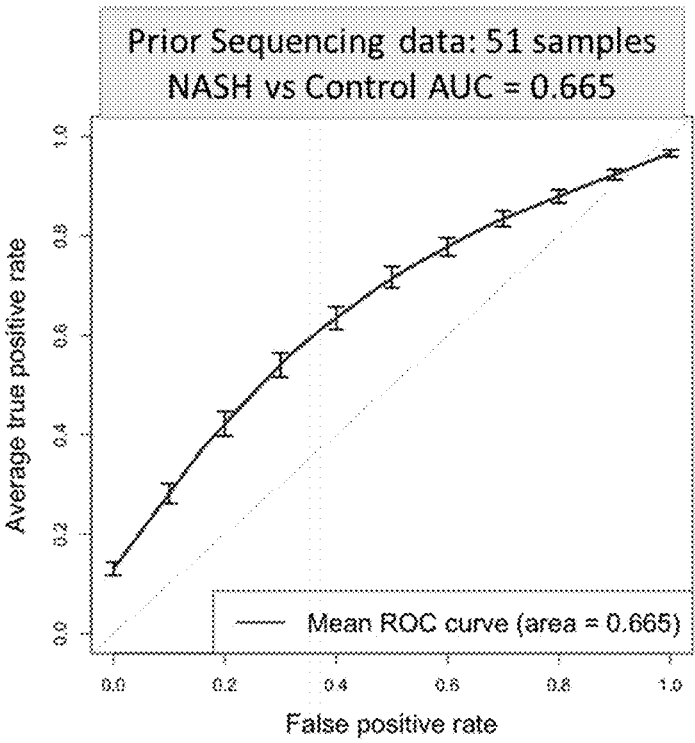
FIG. 17A-B show sequencing assay improvement result in better classifier for NASH vs Control, FIG. 17A before improvements, FIG. 17B after improvements.
Figure 17B:
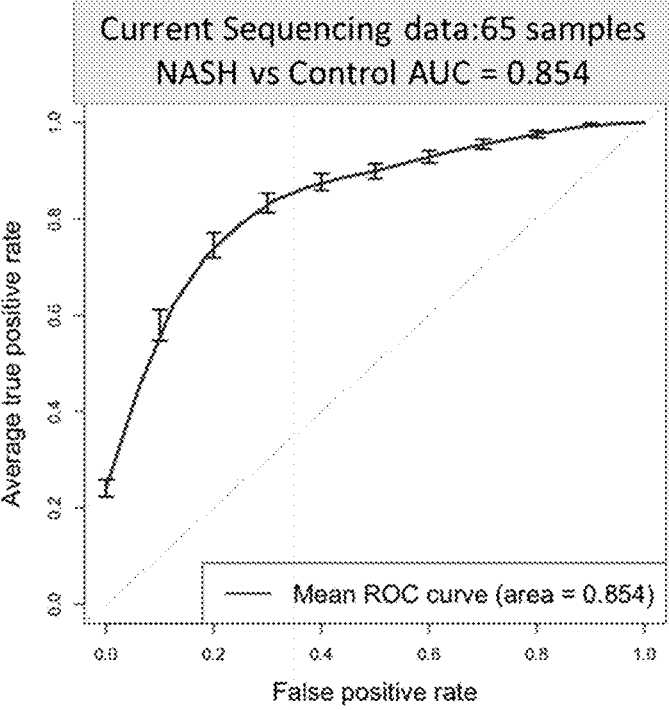

FIG. 16: right panel contains all of the improvements previously discussed: 1) Switching from "Molstract" to new extraction (CNA) kit, 2) addition of polyphenol inhibitor removal column, 3) switching from Clontech Smarter to Swift 1s library preparation. 4) Switching from uniplex capture enrichment to multiplex (16 sample) capture enrichment.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising:
a) obtaining a blood sample from a subject;
b) removing cells from the blood sample to obtain a cell-depleted sample;
c) selectively removing extracellular microparticles originating from blood cells from the cell-depleted sample to obtain an extracellular microparticle-depleted sample, wherein extracellular microparticles not originating from blood cells are not removed from the cell-depleted sample; and
d) assaying the extracellular microparticle-depleted sample to determine an amount of cell-free ribonucleic acid (RNA) corresponding to a gene in the extracellular microparticle-depleted sample.

2. The method of claim 1, wherein selectively removing the extracellular microparticles originating from blood cells further comprises contacting the cell-depleted sample with a binding moiety that interacts with a protein on a surface of the extracellular microparticles originating from blood cells.

3. The method of claim 2, wherein the binding moiety is an antibody or an antigen-binding antibody fragment.

4. The method of claim 3, wherein the antibody or the antigen-binding antibody fragment interacts with a cell surface marker expressed by the blood cells.

5. The method of claim 3, wherein the antibody comprises an anti-Cluster of Differentiation 45 (CD45) antibody.

6. The method of claim 3, wherein the antibody comprises an anti-Cluster of Differentiation 66 (CD66b) antibody.

7. The method of claim 1, further comprising contacting the cell-depleted sample with a first antibody that interacts with a first protein on a first cell and a second antibody that interacts with a second protein on a second cell.

8. The method of claim 7, wherein the first protein is not expressed on the second cell, and wherein the second protein is not expressed on the first cell.

9. The method of claim 1, wherein the extracellular microparticles originating from blood cells comprise exosomes.

10. The method of claim 1, wherein the blood cells comprise platelets, and wherein selectively removing the extracellular microparticles originating from blood cells further comprises contacting the cell-depleted sample with an anti-Glycophorin A (GypA) antibody or a GypA antigen-binding antibody fragment thereof.

11. The method of claim 1, wherein the blood cells comprise red blood cells, and wherein selectively removing the extracellular microparticles originating from blood cells further comprises contacting the cell-depleted sample with an anti-Cluster of Differentiation 235a (CD235a) antibody or a CD235a antigen-binding antibody fragment thereof.

12. The method of claim 1, wherein the blood cells comprise granulocytes, and wherein selectively removing the extracellular microparticles originating from blood cells further comprises contacting the cell-depleted sample with an anti-CD66b antibody or a CD66b antigen-binding antibody fragment thereof.

13. The method of claim 1, wherein the blood cells comprise lymphocytes, and wherein selectively removing the extracellular microparticles originating from blood cells further comprises contacting the cell-depleted sample with an antibody or an antigen-binding antibody fragment thereof that binds to CD45, Cluster of Differentiation 19 (CD19), or Cluster of Differentiation 3 (CD3).

14. The method of claim 1, wherein the cell-depleted sample is incubated for 1 hour at about 60 degrees Celsius.

15. The method of claim 14, further comprising incubating the cell-depleted sample in the presence of a chaotropic salt, a detergent, proteinase K, a 2-mercaptoethanol, or a combination thereof.

16. The method of claim 15, further comprising incubating the cell-depleted sample with Tris(hydroxymethyl)aminomethane (Tris).

17. The method of claim 1, further comprising disrupting lipidic and proteinaceous structures.

18. The method of claim 1, further comprising contacting the cell-depleted sample with a silica column.

19. The method of claim 18, further comprising incubating the cell-depleted sample with a chaotropic salt and isopropanol to enhance binding of RNA to the silica column.

20. The method of claim 1, further comprising incubating the cell-depleted sample with deoxyribonuclease (DNAse) to remove deoxyribonucleic acid (DNA) molecules.

21. The method of claim 1, further comprising removing microRNA, ribosomal RNA, transfer RNA, or a combination thereof, from the cell-depleted sample.

22. The method of claim 1, further comprising determining a gene expression profile of the subject, based at least in part on the amount of cell-free RNA corresponding to the gene.

23. The method of claim 22, further comprising determining a difference between the gene expression profile of the subject and a reference gene expression profile of a reference subject.

* * * * *